United States Patent
Young et al.

(10) Patent No.: US 7,027,970 B2
(45) Date of Patent: Apr. 11, 2006

(54) TOOL FOR IN VITRO-IN VIVO CORRELATION

(75) Inventors: David Young, Ellicott City, MD (US); Sian E. Bigora, Gambrills, MD (US); Leonid V. Gibiansky, North Potomac, MD (US); William R. Gillespie, Apex, NC (US); Theresa A. Shepard, Burnham (GB); Colm B. Farrell, Marlow (GB)

(73) Assignee: Globomax LLC, Hanover, MD (US)

( * ) Notice: Subject to any disclaimer, the term of this patent is extended or adjusted under 35 U.S.C. 154(b) by 701 days.

(21) Appl. No.: 10/274,649

(22) Filed: Oct. 18, 2002

(65) Prior Publication Data

US 2003/0078761 A1    Apr. 24, 2003

Related U.S. Application Data

(60) Provisional application No. 60/344,760, filed on Oct. 19, 2001.

(51) Int. Cl.
G06G 7/58 (2006.01)

(52) U.S. Cl. .............................. 703/11; 702/5; 702/420

(58) Field of Classification Search ................. 703/11; 702/19; 708/5, 315, 420, 813; 435/287.1
See application file for complete search history.

(56) References Cited

U.S. PATENT DOCUMENTS

| | | | | |
|---|---|---|---|---|
| 6,022,733 A | * | 2/2000 | Tam et al. | ................ 435/287.1 |
| 6,761,904 B1 | * | 7/2004 | Bertelsen et al. | ............ 424/464 |
| 6,799,123 B1 | * | 9/2004 | Hughes | ........................ 702/25 |

OTHER PUBLICATIONS

Langenbucher, Handling of computational in vitro/in vivo correlation problems. European Journal of Pharmaceutics, Jan. 2005.*

Williams, In vitro studies replacing in vivo measurement absorption studies. Environmental Toxicology & Pharmacology, Aug. 2005.*

* cited by examiner

*Primary Examiner*—Albert W. Paladini
(74) *Attorney, Agent, or Firm*—Armstrong, Kratz, Quintos, Hanson & Brooks, LLP

(57) ABSTRACT

A biological modeling system and method for enhanced computer-aided analysis of biological response data provides information synthesized from immediate and extended release in vivo data and in vitro data. An executable model of a biological system is developed from information and structures based on the data. In a preferred embodiment, a two stage approach to modeling is used in the development of an IVIVC. The first stage of the procedure is deconvolution, where the percentage of drug absorbed is determined. In the second stage, the in vivo percentage absorbed data is correlated to the in vitro fraction or percentage dissolved data. This correlation then represents a point-to-point relationship between the in vitro dissolution and the in vivo input rate of the drug from the dosage form. In such a correlation, the in vitro dissolution and in vivo absorption profiles are either directly superimposable or may be made to be superimposable by the use of a scaling factor. Prior to the deconvolution stage, a unit impulse response function can be determined from immediate-release concentration-time data. This impulse response function is used in the deconvolution process to determine the in vivo percent absorbed for the extended release formulations. A nonlinear IVIVC model is developed that can incorporate time-scaling and time-shifting into the model if needed. After the two-stage modeling is completed, the predictability of the developed IVIVC model is evaluated by both internal and external validation.

23 Claims, 20 Drawing Sheets

TOOL FOR IN VITRO-IN VIVO CORRELATION

CROSS REFERENCE TO RELATED APPLICATIONS

This application claims priority to U.S. provisional patent application Ser. No. 60/344,760 filed Oct. 19, 2001, the entire contents which are incorporated herein by reference.

BACKGROUND OF THE INVENTION

1. Field of the Invention

This invention pertains generally to data processing for biological systems. More specifically, the present invention is a pharmacokinetics system for correlating in vitro and in vivo data and more particularly to a single tool to conduct these types of studies.

2. Description of the Related Art

Many prior art methods of obtaining biological process data require time consuming laboratory experiments. Data is usually obtained from live animal experiments and clinical trials which are costly and provide many difficult-to-control variables that may mask biochemical activities which are the response of interest. The complexity oft information does not always provide a clear and consistent picture from which accurate conclusions can be drawn.

In an effort to provide more clear and consistent test results, clinical trials are typically designed to isolate a single variable, and use a placebo control group as a baseline from which the variable is measured. Observations from a clinical trial are used to attempt to draw conclusions from apparent differences between the control group and the experimental group. These observations, however, rarely take into account the multi-variable dynamic nature of the patients, either individually or as a group. Such variations are, however, reflected in the data and require large test populations to deal with in an appropriate statistical manner.

A typical cycle for a clinical trial requires years of work. Designing the trial may take six months, performance of the trial may take a year, and analysis of the results may take yet another six months. After years of testing, the results may still be suspect. Additionally, a trial may be one of several ongoing trials necessary to address the variables associated with a particular area of investigation.

Only after numerous costly trial-and-error clinical trials, and constant redesigning of the clinical use of the drug to account for lessons learned from the most recent clinical trial, is a drug finally realized that has adequate safety and efficacy. This process of clinical trial design and redesign, multiple clinical trials and, in some situations, multiple drug redesigns, requires much time and money. Even then, the effort may not produce a marketable drug.

Owing to the cost and difficulty of the experiments, drugs that may be cost-effectively researched and developed using this type of modeling are few. They generally include either refinements to existing drugs, or an attempt to develop a drug for a new application that was inferred from observations made during previous clinical trials and experiments. The enormous risk prevents the development of pharmaceuticals for anything but an extremely large segment of the population. Biological abnormalities which may be treatable by a drug may not be explored, because the potential market for the drug does not justify the expenditure of resources necessary to design, test, and obtain approval for the drug. Even with large market segments, development is extremely speculative. In summary, the cost of drug development is very high and difficult to justify except for the largest of patient populations and lowest of risks.

Pharmacokinetic studies are used to assess the systemic exposure of administered drugs and factors likely to affect this exposure. The studies are desirably carried out in a well-controlled clinical environment. Samples are collected on each of the study subjects, and concentration-time data are analyzed to derive parameters such as the observed maximum concentration, Cmax, and the area under the concentration-time curve, AUC.

The statistical analysis of pharmacokinetic data addresses time-dependent repeated measurements of drug of concentrations in various organs of the body, with the goal to describe the time course and to determine clinically relevant parameters by modeling the organism through compartments and flow rates. The mathematical solution is a system of differential equations with an explicit solution for most of the one or two compartment models. Otherwise, numerical solutions have to be used. Intrinsic pharmacokinetic parameters include area under the curve (AUC), clearance, distribution volume, half time, elimination rates, minimum inhibitory concentrations, etc.

In addition to the prior art in vivo studies, a number of in vitro or cell culture-based methods have been described for identifying compounds with a particular biological effect. From these trials and experiments, data is obtained which usually focuses on a more specific part of the biological system, and avoids some oft variables that cannot otherwise be controlled. While conclusions may be drawn by assimilating experimental data and published information, it is difficult, if not impossible, for an individual or research team to synthesize the relationships among all the available data and knowledge. Consequently, it is highly desirable to provide advanced tools and techniques which enable the individual or research team to study whether there is a correlation between the data obtained from the testing methods. These correlations are important from the early development stages throughout the entire development and evaluation cycle. The data and the developed correlations are used to assist the scientist in understanding and optimizing pharmaceutical formulations. The FDA has recognized the utility of In Vitro In Vivo Correlation, hereinafter "IVIVC", and has provided guidance pertaining thereto. The guidance provides recommendations to sponsors of new drug applications (NDA's), abbreviated new drug applications (ANDA's), and abbreviated antibiotic applications (AADA's). Specifically addressed are the Scale-Up and Post Approval Changes (herein after "SUPAC"), and notification requirements. IVIVC results can be utilized in the following development conditions: 1) As a surrogate to expensive bioequivalency studies, which may typically be required for SUPAC changes for instances involving minor manufacturing, formulation or strength changes; 2) To support and/or validate the use of dissolution testing and specifications as range setting parameters for quality control tool to measure process control; 3) To serve as a prediction toll to predict the in-vivo performance of a formulation using in-vitro dissolution data which can be applied to formulation design specifications in order to achieve optimal plasma concentration-time profiles; 4) To identify appropriate dissolution characteristics for a particular formulation which result in data relevant to in vivo performance. Within this guidance is the identification of situations where IVIVC data is acceptable in lieu of in vivo bioequivalence testing. What is needed then is an improved system and method which more efficiently reveals and conveys correlations between in vivo and in vitro results of tests performed on complex biological systems, which may be used by artisans in product development and in meeting governmental requirements.

SUMMARY OF THE INVENTION

The present invention provides a method and apparatus which allows correlation between in vivo and in vitro data. A model can be built to simulate individual patients or specific groupings of patients, or the general population as a whole. Once the model is created in the modeling tool, the model must be run and balanced to accurately reflect observed phenomenon. Balancing in the prior art is extremely time consuming and labor intensive, requiring tedious input to represent knowledge not available in the stored models. This knowledge alters the model from one with less real world correlation to one that accurately reflects the clinical behaviors. The balancing process can help to identify inconsistencies in knowledge stored in the database.

Before and after the model is run, each observable characteristic or data item should be checked against corresponding real world data. For example, a particular piece of literature may deal with a particular biological system of the model. This may be checked for accuracy against the real world information disclosed in the literature. Changes may be made to the model repeatedly.

Once the model exhibits reasonable performance, the values of the outputs are re-interpreted and mapped into values that correlate with actual clinical outcomes. The model is then systematically run and tested using a set of matrices on which clinical and experimental data are recorded. The model is run repeatedly, systematically altering the various input data and recording the various internal outputs of the model, to ensure that the outcomes of the model make sense. A redesign and/or a re-balancing of certain portions of the model may need to be made at this point to ensure proper behavior under the various key situations of interest. The correlations between in vitro and in vivo testing that are identified by the preferred model help to optimize the development of pharmaceutical formulations, and are useful in the application of IVIVC, SUPAC and Biowaiver principles.

In a first manifestation, the invention is a computer executable model of a biological system in combination with a computer system including a memory and a processor. The computer executable model has a plurality of biological representations stored in memory as a plurality of chemical level data points, each chemical level data point representing a level of a chemical within a particular time period in a biological component. A means exists for determining unit impulse response from a first collection of the plurality of biological representations. Another means performs deconvolution, having as inputs unit impulse response and a second collection of the plurality of biological representations. The deconvolution means produces as an output in vivo mean absorption data. A means is provided for developing an in vitro in vivo correlation model that uses as inputs a third collection of the plurality of biological representations, each of the third collection of said plurality of biological representations chemical level data points representing in vitro ER data and in vivo mean absorption data. A means is also provided for validation of the in vitro in vivo correlation model.

In a second manifestation, the invention is a method for processing biological profile data for in vitro in vivo correlation. The steps of the method include storing a plurality of biological profiles in a computer memory in computer readable form, each biological signal profile in ones of the plurality of biological signal profiles comprising a plurality of data points, each data point representing a measurement of a chemical level. A unit impulse response is determined from a first one of the biological profiles. Deconvolution is performed on a second one of the biological profiles using the unit impulse response, to produce in vivo mean absorption data. An in vitro in vivo correlation model is developed using the in vivo mean absorption data and an in vitro ER data biological signal profile; and the in vitro in vivo correlation model is validated.

OBJECTS OF THE INVENTION

A first object of the invention is to provide a system and method for modeling biological systems that may be used throughout product development. A second object of the invention is to provide a system and method for modeling biological systems in a manner reflecting the dynamic and multi-variable nature of the systems. A third object of the invention is to provide a method for drug development which provides in vitro in vivo correlations. Another object of the invention is to facilitate problem specification and model definition. Yet another object of the invention is to enable a user to conduct all analyses within one tool. These and other objects are achieved in the present invention, which may be best understood by the following detailed description and drawings of the preferred embodiment.

DESCRIPTION OF THE PREFERRED EMBODIMENT

Figure 1:
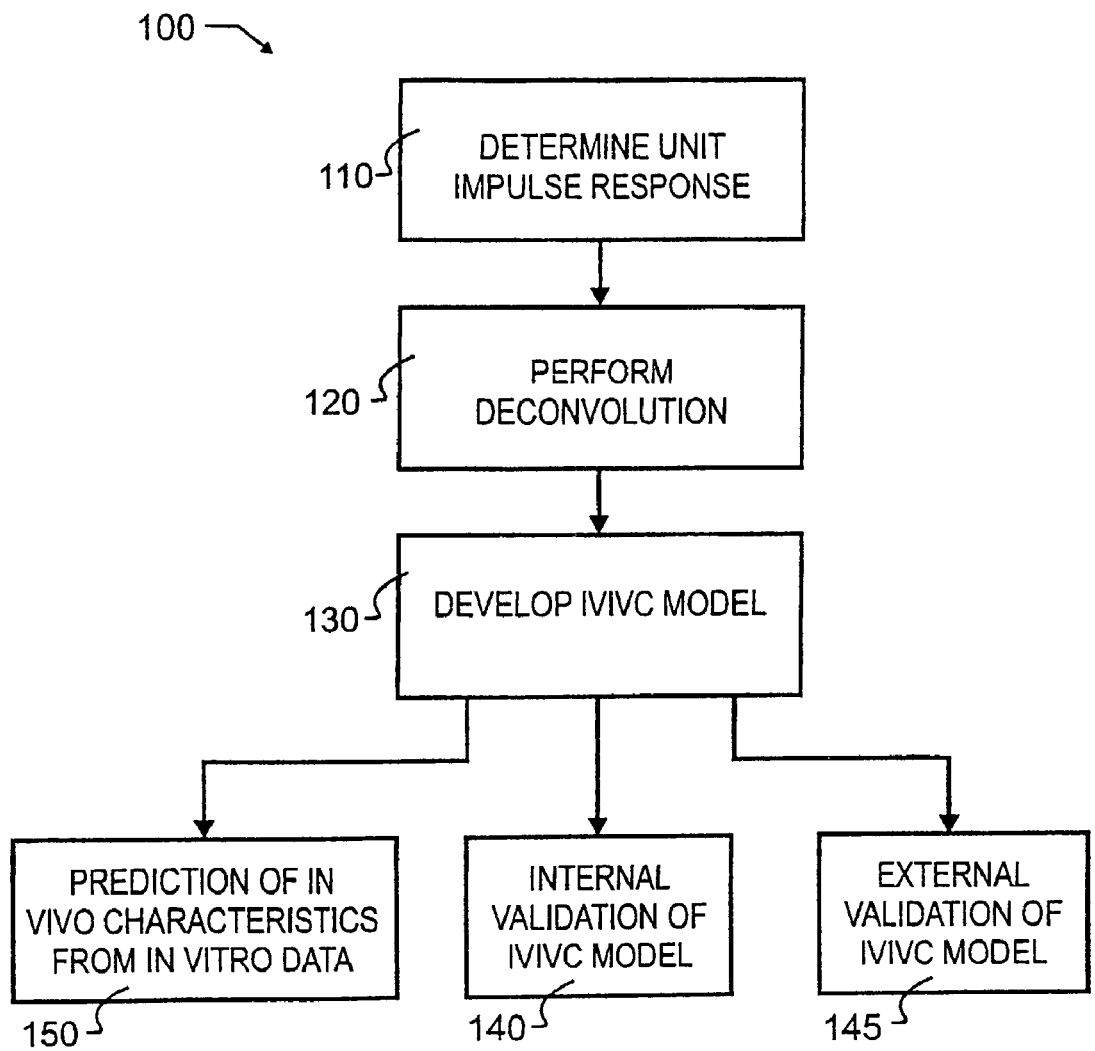
FIG. 1 illustrates the major processes associated with a preferred method in accord with the teachings of the present invention.

A preferred embodiment IVIVC pharmacokinetic modeling and analysis method 100 showing the major processes is illustrated in FIG. 1 by simplified block diagram. As illustrated therein, preferred method 100 comprises a total of four primary processes, and two independent processes that may or may not use information provided or generated in the four primary processes.

The four primary processes include determining unit impulse response in process 110, the two stages of IVIVC model development which include the process of performing deconvolution 120 and the process of developing the IVIVC model 130, and subsequent to IVIVC model development, the process of internal validation 140. A unit impulse response function can be determined from immediate-release concentration-time data in process 110. This impulse response function is used in the deconvolution process 120 to determine the in vivo percent absorbed for the extended release formulations. A nonlinear IVIVC model is developed in process 130 the in vivo percentage absorbed data is correlated to the in vitro fraction or percentage dissolved data. This correlation then represents a point-to-point relationship between the in vitro dissolution and the in vivo input rate of the drug from the dosage form. In such a correlation, the in vitro dissolution and in vivo absorption profiles are either directly superimposable or may be made to be superimposable by the use of a scaling factor. Both time-scaling and time-shifting may be incorporated into the model if needed. The evaluation of the predictability of the developed IVIVC model may be accomplished by internal validation in process 140.

The two independent processes illustrated in FIG. 1 include the prediction of in vivo characteristics from in vitro data in process 150, and the evaluation of the predictability of the developed IVIVC model by external validation in process 145. Each of these primary and independent processes 110–150 are described herein below in greater detail, with reference to illustration FIGS. 5–19.

Figure 2:
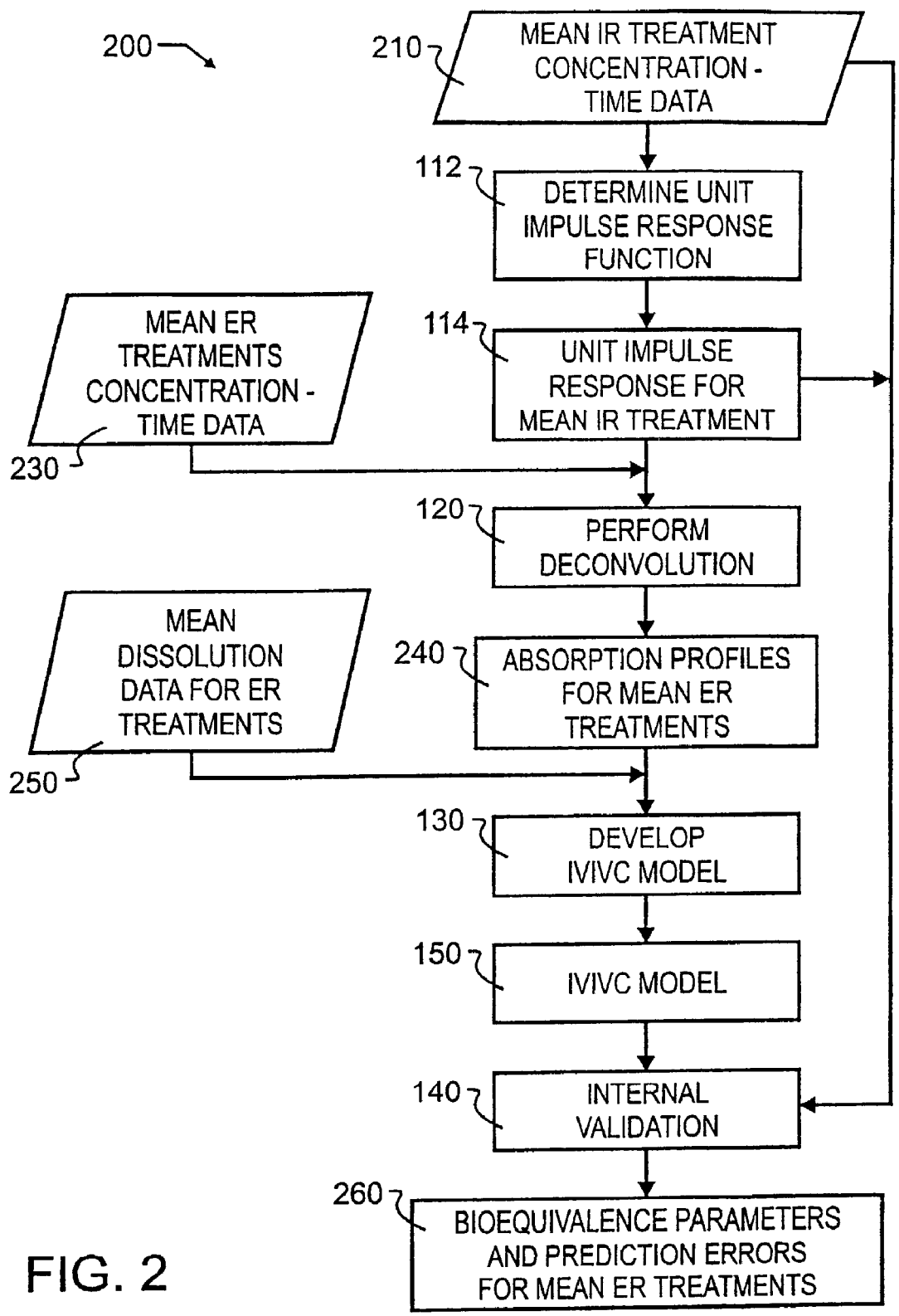
FIG. 2 illustrates a preferred method multiple modeling approach, using mean data throughout the IVIVC model development and validation, which demonstrates the teachings of the present invention.
Figure 3:
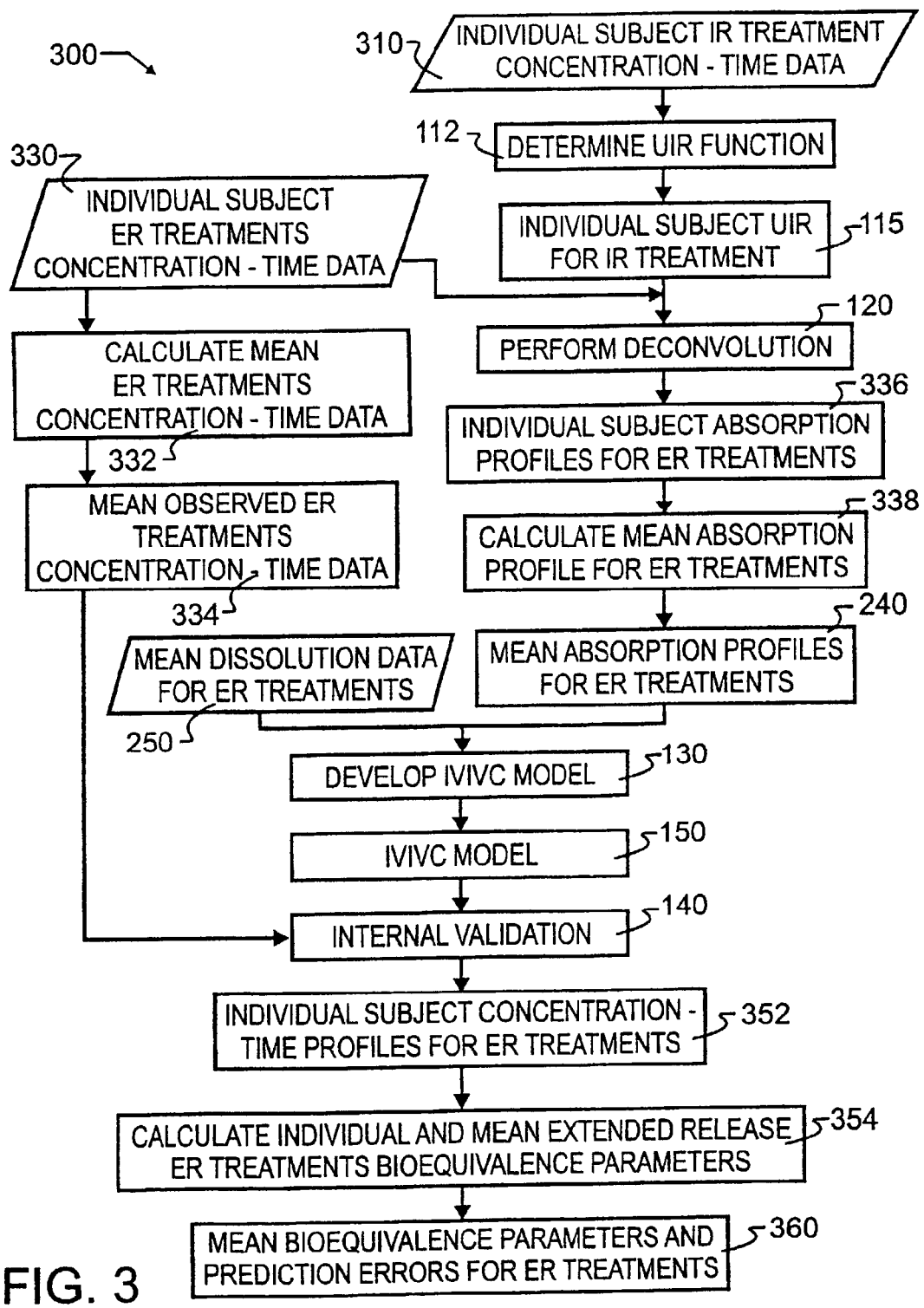
FIG. 3 illustrates a preferred method multiple modeling approach, using a combination of individual subject and mean data in the IVIVC model development and validation, which demonstrates the teachings of the present invention.
Figure 4:
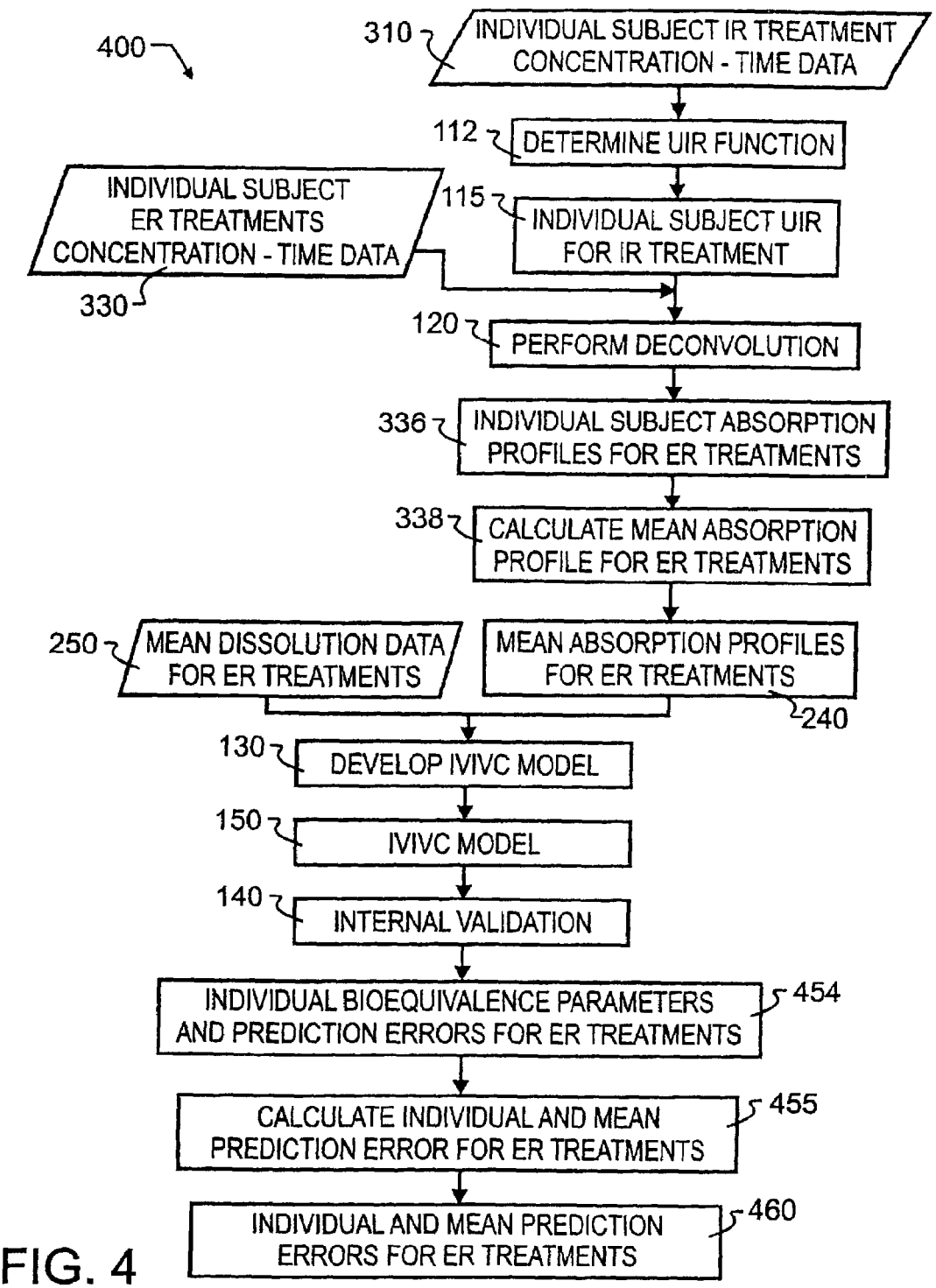
FIG. 4 illustrates a preferred method multiple modeling approach, using individual subject data in the IVIVC model development and validation, which demonstrates the teachings of the present invention.

Specific methods of implementing the preferred method 100 of IVIVC correlation are shown in FIGS. 2–4 as methods 200, 300 and 400, but these will be understood to illustrative of only a few of the preferred embodiments that are contemplated, and are consequently only exemplary in nature only and not limiting to the scope of the present invention. FIG. 2 illustrates a preferred method 200 multiple modeling approach, using mean data throughout the IVIVC model development and validation. In step 210, mean in vivo Impulse Response (hereinafter "IR") treatment concentration—time data is either imported, entered, or otherwise provided. Next, using process 110, at step 112 the Unit Impulse Response function (hereinafter "UIR") is determined and at step 114 the UIR for mean IR treatment is determined. The UIR for mean IR treatment derived from step 114 is used together with the mean Extended Release (herein after "ER") treatments in vivo concentration—time data 230 which is imported, entered, or otherwise provided, to perform deconvolution process 120. The results of deconvolution process 120 are absorption profiles for mean ER in vivo treatments 240. In vivo absorption profiles 240 are used together with mean dissolution data for ER treatments 250 which is imported, entered, or otherwise provided, to develop the IVIVC model using process 130. Once the IVIVC model is developed, it will preferably be run using process 150 to provide a prediction of in vivo characteristics from in vitro data. This information will preferably be used in step 140 to provide internal validation of the IVIVC model. Finally, in step 260, bioequivalence parameters and prediction errors for mean ER treatments are generated. While only selectively illustrated and even then, only in FIG. 2, internal validation process 140 may be used not only with respect to the IVIVC model, but also with various data that is used in the preferred method 100. This is illustrated diagrammatically in FIG. 2 by the lines extending from steps 210 and 114 to internal validation process 140.

FIG. 3 illustrates a preferred method 300 multiple modeling approach, using a combination of individual subject and mean data in the IVIVC model development and validation. In step 310, individual subject in vivo IR treatment concentration—time data is either imported, entered, or otherwise provided. Next, using process 110, at step 112 the UIR is determined and at step 115 the individual subject UIR for IR treatment is determined. The UIR for IR treatment derived from step 115 is used together with the individual subject ER treatments in vivo concentration—time data 330 which is imported, entered, or otherwise provided, to perform deconvolution process 120. The results of deconvolution process 120 are individual subject absorption profiles for ER in vivo treatments 336. From these, the mean absorption profile for ER treatments 240 is calculated at step 338. In vivo mean absorption profiles 240 are used together with mean dissolution data for ER treatments 250 which is imported, entered, or otherwise provided, to develop the IVIVC model using process 130. Once the IVIVC model is developed, it will preferably be run using process 150 to provide a prediction of in vivo characteristics from in vitro data. This information will preferably be used in step 140 to provide internal validation of the IVIVC model. This method 300 illustrates additional validation which may be obtained from the individual subject ER treatments in vivo concentration—time data 330. As illustrated, data 330 is used to calculate mean ER treatments in vivo concentration—time data in step 332, to provide mean observed ER treatments in vivo concentration—time data 334. Mean observed ER treatments in vivo concentration—time data 334 may be compared with the results for process 150 to provide the additional validation. After validation step 140, individual subject concentration—time profiles for ER treatments 352 are determined, and in step 354 individual and mean ER treatments bioequivalence parameters are calculated. The results are mean bioequivalence parameters and prediction errors for each ER treatment 360.

FIG. 4 illustrates a preferred method 400 multiple modeling approach, using individual subject data in the IVIVC model development and validation, which demonstrates the teachings of the present invention. In this method 400, in step 310, individual subject in vivo IR treatment concentration—time data is either imported, entered, or otherwise provided. Next, using process 110, at step 112 the UIR is determined and at step 115 the individual subject UIR for IR treatment is determined. The UIR for IR treatment derived from step 115 is used together with the individual subject ER treatments in vivo concentration—time data 330 which is imported, entered, or otherwise provided, to perform deconvolution process 120. The results of deconvolution process 120 are individual subject absorption profiles for ER in vivo treatments 336. From these, the mean absorption profile for ER treatments 240 is calculated at step 338. In vivo mean absorption profiles 240 are used together with mean dissolution data for ER treatments 250 which is imported, entered, or otherwise provided, to develop the IVIVC model using process 130. Once the IVIVC model is developed, it will preferably be run using process 150 to provide a prediction of in vivo characteristics from in vitro data. This information will preferably be used in step 140 to provide internal validation of the IVIVC model. After validation step 140, Individual bioequivalence parameters and prediction errors for ER treatments are used in step 455 to calculate individual and mean prediction errors for ER treatments. The results are individual and mean prediction errors for ER treatments 460.

Figure 5:
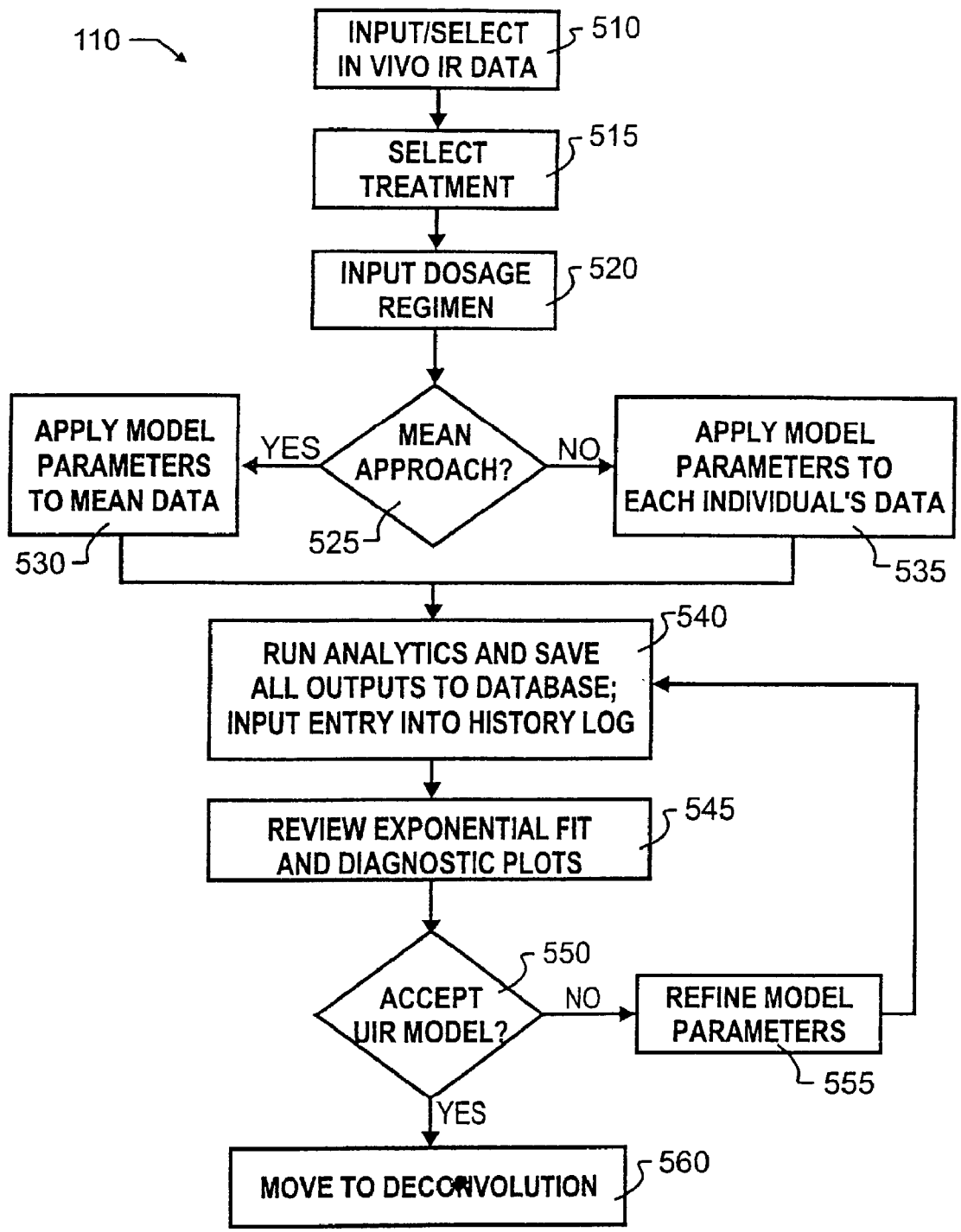
FIG. 5 illustrates in greater detail the preferred process for determining unit impulse response identified in FIG. 1.

FIG. 5 illustrates in greater detail the preferred process 110 for determining unit impulse response. A user will begin process 110 by either providing or selecting in vivo IR data in step 510. The data may be provided by importing a data file, keyboard input, or other means. Next, the user will select treatment in step 515, to be identified as the IR or faster release product as compared to the ER treatments to be used in the deconvolution process 120. The user then inputs the dosage regimen, identifying whether the dose is a single or multiple dose regimen. In step 525, the user will select whether the approach used will be a mean approach, in which case process 110 will apply model parameters to mean data in step 530, and, if not a mean approach, process 110 will apply model parameters to each individual's data in step 535. At this point, the process is ready to be executed in step 540, which will determine a UIR. In the preferred embodiment, this is accomplished by estimating a polyexponential function to describe the pharmacokinetic characteristics of the immediate release data. The polyexponential impulse response function $c_\delta(t)$ is approximated by:

$$c_\delta(t) = \Sigma_i a_1 \exp(\alpha_1(t-t_0)) \; t \geq t_0 \quad (1)$$

$$c_\delta(t) = 0, \; t < t_0 \quad (2)$$

where $t_0$ is a common lag time. If it is known that $c_\delta(t_0)=0$, then $\Sigma_i a_1 = 0$.

Parameters of the exponents are stored in the database as "a, alpha, lagtime" with one row for each exponent. The lag time $t_0$ is the same for all the exponents of the same subject. The program allows different modeling parameters to be applied to each subject's data during the modeling process. Multiple subjects data can be modeled simultaneously. A number of options can be incorporated into the model, including lag time, weighting, maximum exponentials, maximum ratio of a, and the upper limit for $\alpha$. During the UIR modeling process, in the most preferred embodiment, an iterative weighted least square method is used where the sum of residuals squares is weighted by the universe predicted concentration value, and the iterative fits are performed starting with the highest number of exponents chosen and then n−1, n−2, n−3, etc. The fit with the lowest AIC value is considered the best fit and returned as the unit impulse response. Once the analytical calculations are run, step 540 will save all outputs to the database; and make an input entry into the history log. The results are ready to be reviewed, including exponential fit and diagnostic plots in step 545. The user will then decide whether to accept the UIR model. If not, the user will refine model parameters in step 555, and then re-execute the calculations at step 540. In the alternative, the UIR has been accepted, and process 100 is ready to continue with deconvolution at step 560.

Figure 6:
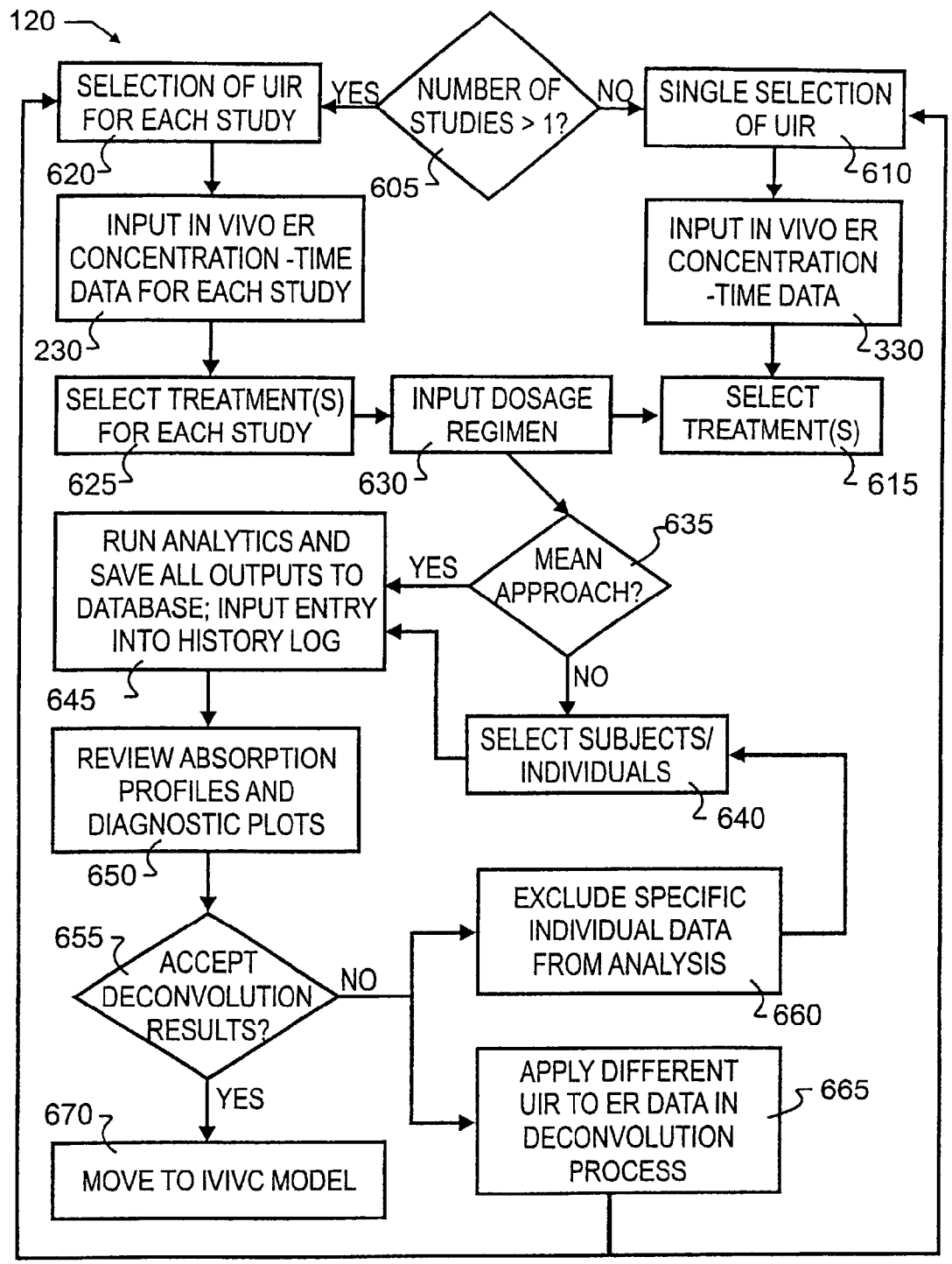
FIG. 6 illustrates in greater detail the preferred process for performing deconvolution identified in FIG. 1.

FIG. 6 illustrates in greater detail the preferred process 120 for performing deconvolution. In this process the percentage of the drug released in vivo relative to the immediate release dose is estimated using a numerical deconvolution approach. The process preferably allows multiple studies and multiple subject data to be modeled simultaneously, and does not require that the unit impulse response be derived from intravenous data. The first step 605 of the deconvolution process 120 is to determine whether one or more studies are to be selected. If a single selection of UIR is made in step 610, the in vivo ER concentration—time data is input at step 330. Finally, the treatments, of the type in step 515, will need to be selected in step 515. If a plurality of studies are chosen in step 605, each of the studies need to be selected in step 620. The in vivo ER concentration—time data for each study is input, and the treatment(s) for each study are selected in step 625. Whether for one or multiple studies, the user will input dosage regimen in step 630, which, similar to step 520, will include whether the dosage is a single or multiple dose regimen. The user next decides whether to use the mean approach in step 635. If not, the user will need to select the subjects or individuals in step 640. The settings have now been established, and deconvolution process 120 will run the analytical calculations and save all outputs to database; and input an entry into the history log in step 645. The user will then review the absorption profiles and diagnostic plots in step 650, and elect whether to accept the deconvolution results at step 655. If the results are not acceptable, and require adjustments, the user will decide whether to apply a different UIR to ER data in step 665, and/or whether to exclude specific individual data from analysis in step 660. Excluding specific individual data in step 660 leads to a new selection at step 640, and process flow continuing again into step 645. If a different UIR is to be applied in accord with step 665, this will force process 120 flow to step 620. Whether the user accepts the deconvolution results on the first pass or on a later try, the ultimate conclusion is to derive suitable results, and then move on to the IVIVC model in step 670.

Figure 7:
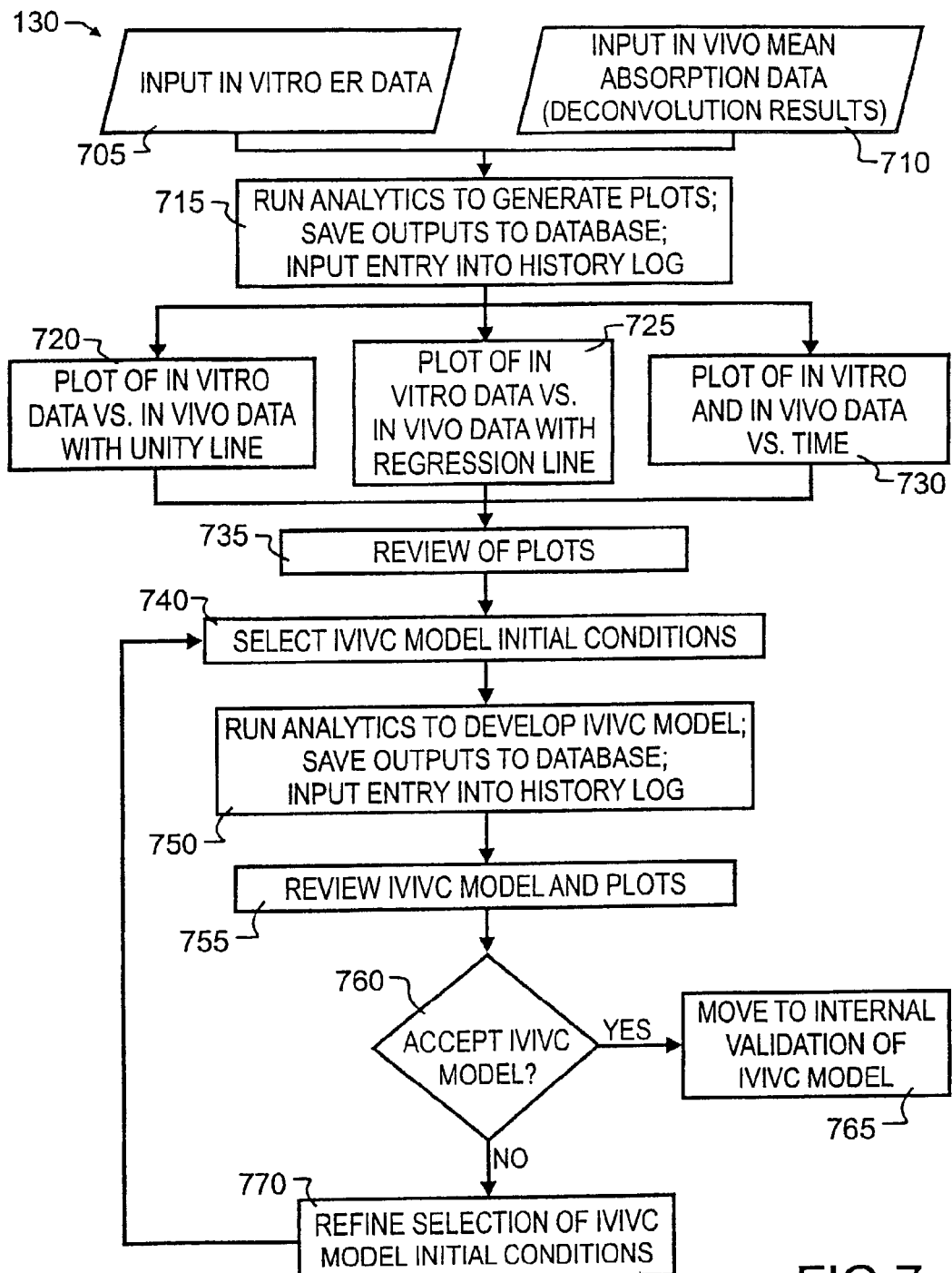
FIG. 7 illustrates in greater detail the preferred process for developing the IVIVC model identified in FIG. 1.

FIG. 7 illustrates in greater detail the preferred process 130 for developing the IVIVC model identified in FIG. 1. This process fits a linear regression model to the in vitro dissolution data and the in vivo release data for each treatment. The best fit is determined based upon the mean square error of the differences between the IVIVC model predicted in vivo release and the observed in vitro release. In one preferred embodiment, the model investigated will be of the following form:

$$X_{vivo(t)} = \begin{cases} 0 & t < 0 \\ & u = t \text{ for } t \leq T \\ a_1 + a_2 \cdot X_{vitro}(-b_1 + b_2 \cdot u) & u = T \text{ for } t > T \end{cases}$$

where:
$X_{vivo}(t)$=the % release in vivo at time (t);
$a_1$ allows for a difference between the initial in vitro and in vivo drug release;
$a_2$=the bioavailability of the extended release formulation relative to immediate release;
$b_1$ allows for a time shift between in vitro and in vivo release;
$b_2$ allows for time scaling between in vitro and in vivo release; and
T=time after which no drug absorption occurs (allows for different bioavailability between ER formulations).

Process 130 for developing the IVIVC model begins with steps 705 and 710, which includes inputting the in vitro ER data and the in vivo mean absorption data from the deconvolution results. Analytics are run in step 715 to generate plots; save outputs to database; and place an input entry into the history log. Preferably, in steps 720, 725, and 730 the preferred process 130 will include plots such as in vitro data vs. in vivo data with unity line; in vitro data vs. in vivo data with regression line; and in vitro and in vivo data vs. time. The user will then review the plots, and from the information obtained select IVIVC model initial conditions. Most preferably, the user will have the option of selecting default values that are provided for each parameter, or alternatively selecting new values for those parameters. The parameters are described herein above, and include the variables $a_1$, $a_2$, $b_1$, $b_2$, and T. Preferably, at this time the user will also decide whether a weighting factor is added to the IVIVC model. After the parameters are set in step 740, the model will be executed, which will include running analytics to develop the IVIVC model; saving outputs to the database; and inputting an entry into the history log in step 750. The user will now, in step 755, review the IVIVC model and plots, to determine whether any changes need to be made. If there are changes required, the user will be given the opportunity to refine selection of the IVIVC model initial conditions in step 770, sending the user subsequently back to step 740. Otherwise, the user elects to accept the IVIVC model at step 760, and then the process will move to internal validation of the IVIVC model at step 765.

An IVIVC should be evaluated to demonstrate that predictability of in vivo performance of a drug product from in vitro dissolution characteristics is maintained over a range of in vitro dissolution release rates and manufacturing changes. The model will most preferably predict the entire in vivo time course from the in vitro data. In context, the model refers to the relationship between in vitro dissolution of an ER dosage form and the in vivo response such as plasma drug concentration or amount of drug absorbed. Since the objective of developing an IVIVC is to establish a predictive mathematical model describing the relationship between an in vitro property and a relevant in vivo response, the proposed evaluation approaches focus on the estimation of predictive performance, or, conversely, prediction error. Depending on the intended application of an IVIVC and the therapeutic index of the drug, evaluation of prediction error internally and/or externally may be appropriate. Evaluation of internal predictability is based on the initial data used to define the IVIVC model, identified as process 140. Evaluation of external predictability is based on additional test data set, identified as process 145.

Figure 8:
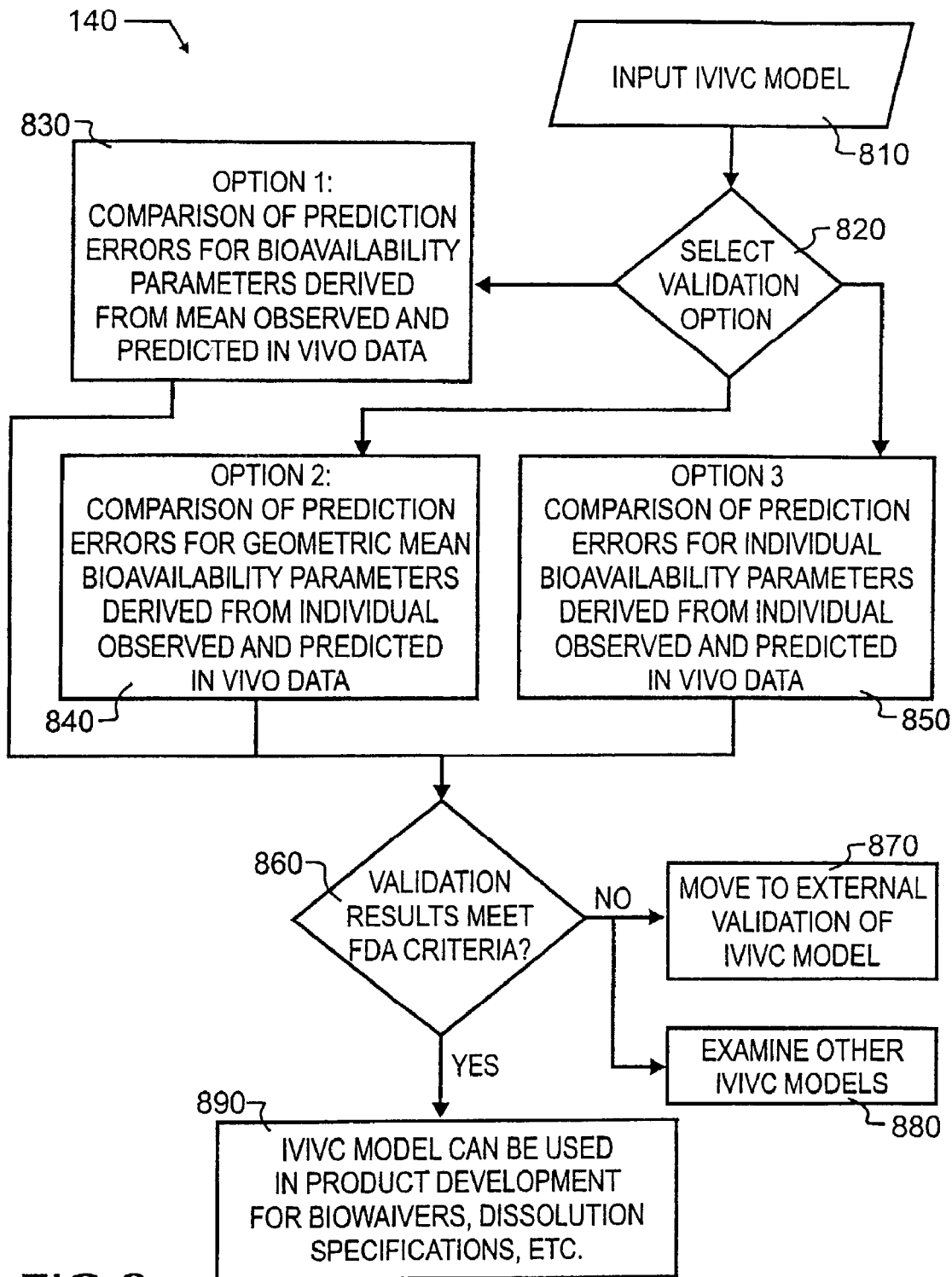
FIG. 8 illustrates in greater detail the preferred process for internal validation of the IVIVC model in FIG. 1.

FIG. 8 illustrates in greater detail the preferred process 140 for internal validation of the IVIVC model. The first step 810 is to input the IVIVC model. Next, the user will be required to select a validation option. The first option 830 is a comparison of prediction errors for bioavailability parameters derived from mean observed and predicted in vivo data. This option is illustrated in more detail in FIG. 9. The second option 840 is the comparison of prediction errors for geometric mean bioavailability parameters derived from individual observed and predicted in vivo data. This option is illustrated in more detail in FIG. 10. The third option 850 is the comparison of prediction errors for individual bioavailability parameters derived from individual observed and predicted in vivo data. This option is illustrated in more detail in FIG. 11. Regardless of the option which is appropriate, the next step is to verify that the validation results meet FDA criteria in step 860. If not, the user will need to either move to external validation of the IVIVC model in step 870 and illustrated as process 145 in more detail in FIG. 12, or examine other IVIVC models in step 880. If the validation results meet FDA criteria in step 860, then the IVIVC model can be used in product development for biowaivers, dissolution specifications, etc. as shown in step 890.

Figure 9:
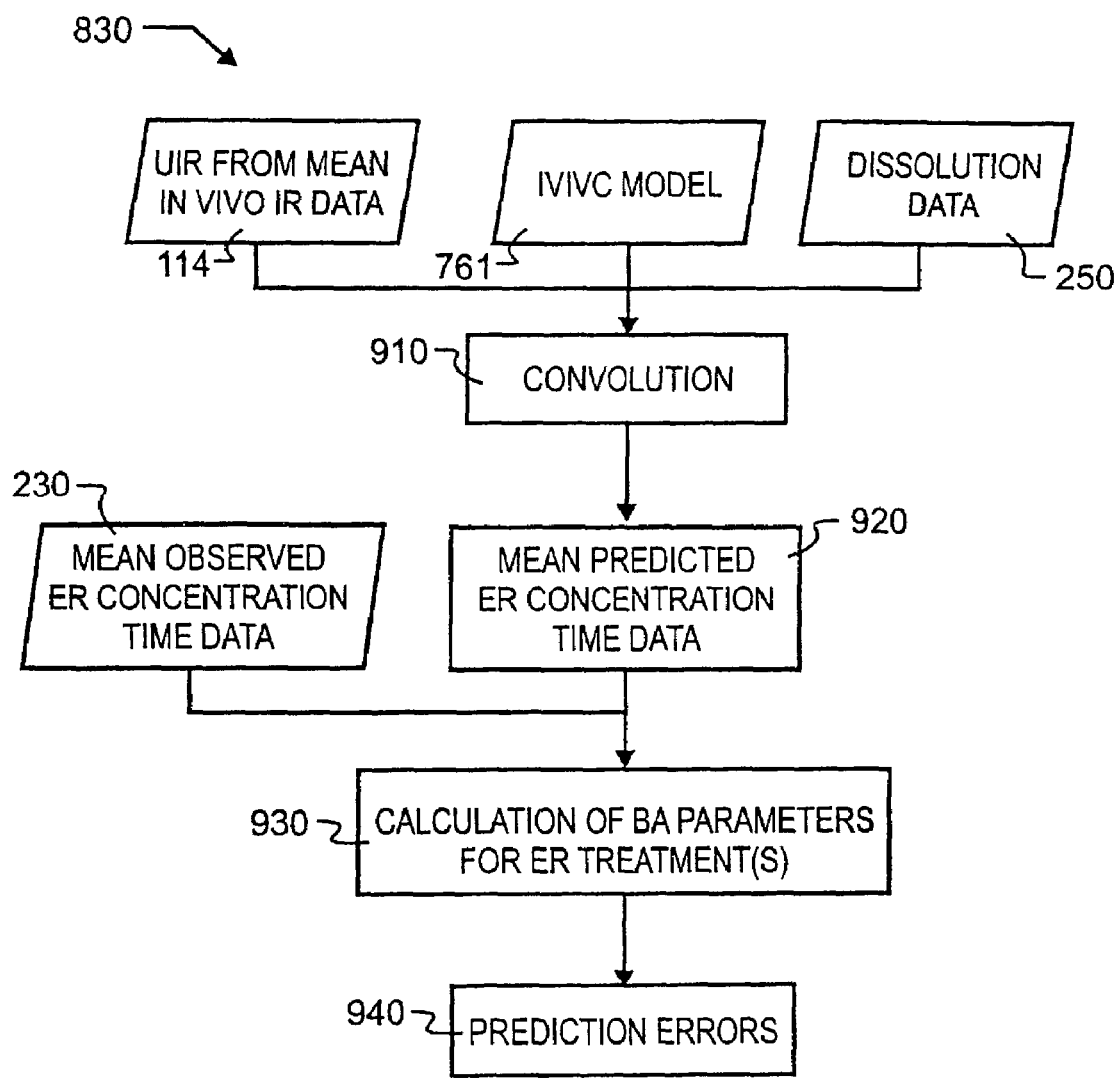
FIGS. 9–11 illustrate in greater detail the preferred validation options identified in FIG. 8.
Figure 10:
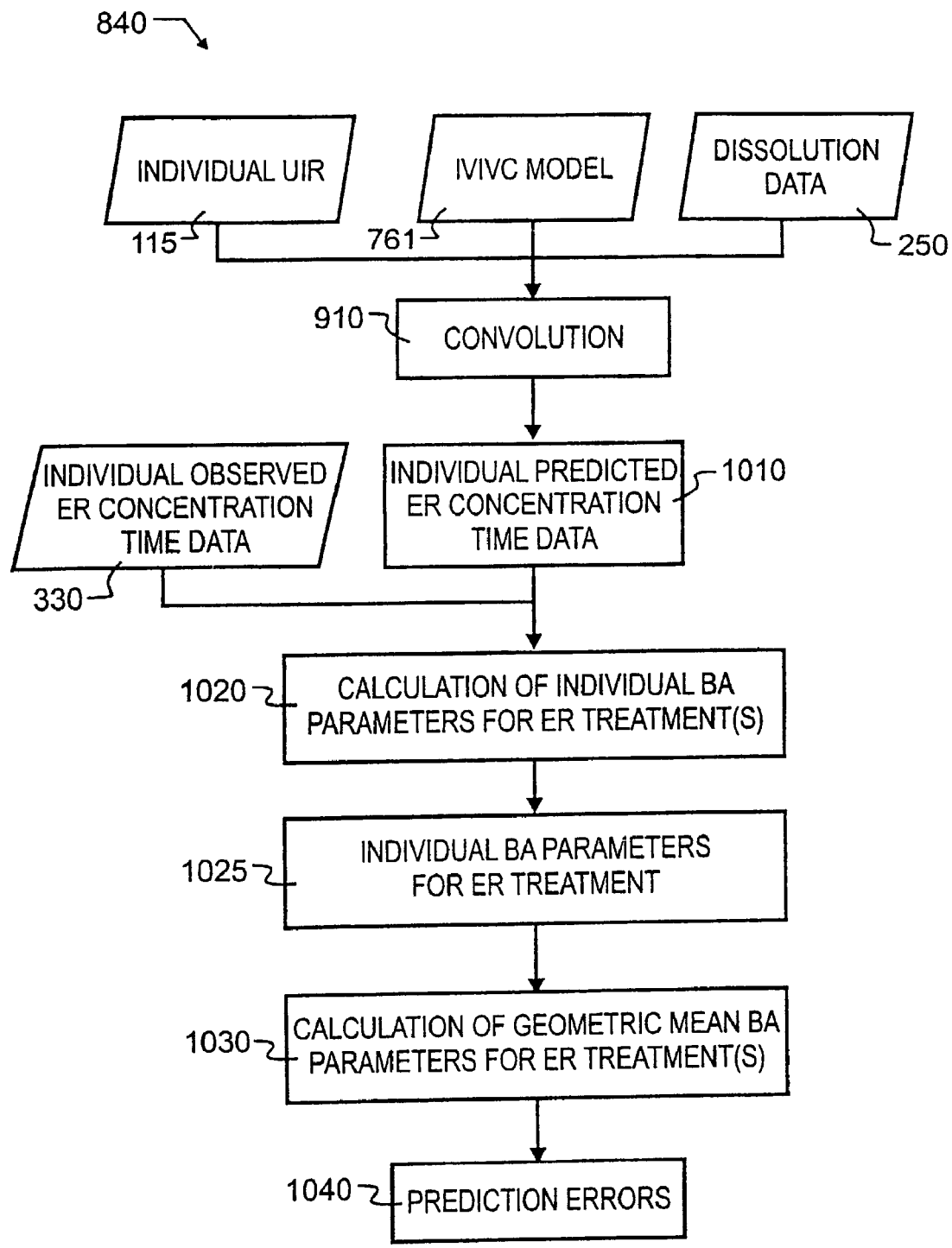
Figure 11:
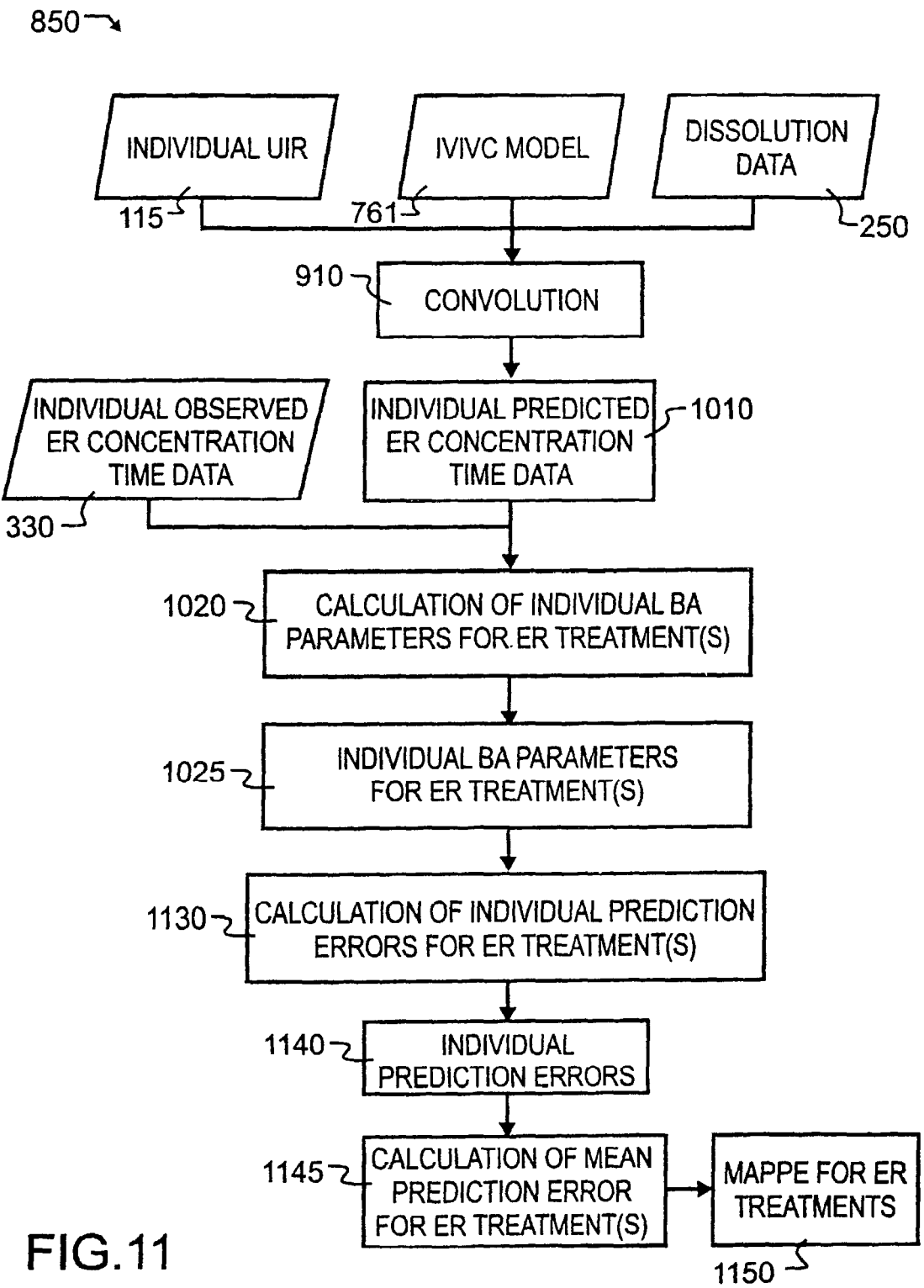

FIGS. 9–11 illustrate in greater detail the preferred validation options identified in FIG. 8. The first option 830 shown in FIG. 9 is a comparison of prediction errors for bioavailability parameters derived from mean observed and predicted in vivo data. Using the process illustrated in this option, the UIR 114 determined from mean in vivo IR data, the IVIVC model 761 accepted at step 760 to be validated, and the in vitro dissolution data 250 are processed in convolution step 910 to provide mean predicted ER concentration time data 920. The mean predicted ER concentration time data 920 and mean observed ER concentration time data 230 are used in step 930 for the calculation of bioavailability (BA) parameters for ER treatment(s). The result of these calculations 930 are prediction errors 940, which are used in the decision whether IVIVC model is validated. One preferred collection of data values includes CMAX and AUC values, both predicted and observed, the ratios of the predicted values to observed, and the mean absolute percentage prediction errors (MAPPE).

The second option 840 is the comparison of prediction errors for geometric mean bioavailability parameters derived from individual observed and predicted in vivo data, illustrated in FIG. 10. Using the process illustrated in this option, the individual UIR 115 determined from individual in vivo IR data, the IVIVC model 761 accepted at step 760 to be validated, and the in vitro dissolution data 250 are processed in convolution step 910 to provide individual predicted ER concentration time data 1010. The individual predicted ER concentration time data 1010 and individual observed ER concentration time data 330 are used in step 1020 for the calculation of individual bioavailability (BA) parameters for ER treatment(s). The result of these calculations 1020 are individual BA parameters for ER treatment(s) 1025. The individual BA parameters for ER treatment(s) 1025 are in turn used in the calculation of geometric mean BA parameters for ER treatment(s) at step 1030, which in turn produces prediction errors 1040.

The third option 850 is the comparison of prediction errors for individual bioavailability parameters derived from individual observed and predicted in vivo data, illustrated in FIG. 11. Using the process illustrated in this option, the individual UIR 115 determined from individual in vivo IR data, the IVIVC model 761 accepted at step 760 to be validated, and the in vitro dissolution data 250 are processed in convolution step 910 to provide individual predicted ER concentration time data 1010. The individual predicted ER concentration time data 1010 and individual observed ER concentration time data 330 are used in step 1020 for the calculation of individual bioavailability (BA) parameters for ER treatment(s). The result of these calculations 1020 are individual BA parameters for ER treatment(s) 1025. The individual BA parameters for ER treatment(s) 1025 are in turn used in the calculation of individual prediction errors for ER treatment(s) at step 1130, which in turn produces individual prediction errors 1140. These individual prediction errors 1140 are used in the calculation of the mean prediction error for ER treatment(s) in step 1145, and then the result is used for a map for ER treatment(s) at step 1150.

In one preferred embodiment, the criteria for establishing internal predictability of the IVIVC model is that the absolute percent prediction error (% PE) to be 10% or less for $C_{max}$ and AUC. In addition, the % PE for each formulation should not exceed 15%. If these criteria are not met, the internal predictability of the IVIVC is inconclusive and evaluation of external predictability of the IVIVC should be performed as a final determination of the ability of the IVIVC to be used as a surrogate for bioequivalence.

Figure 12:
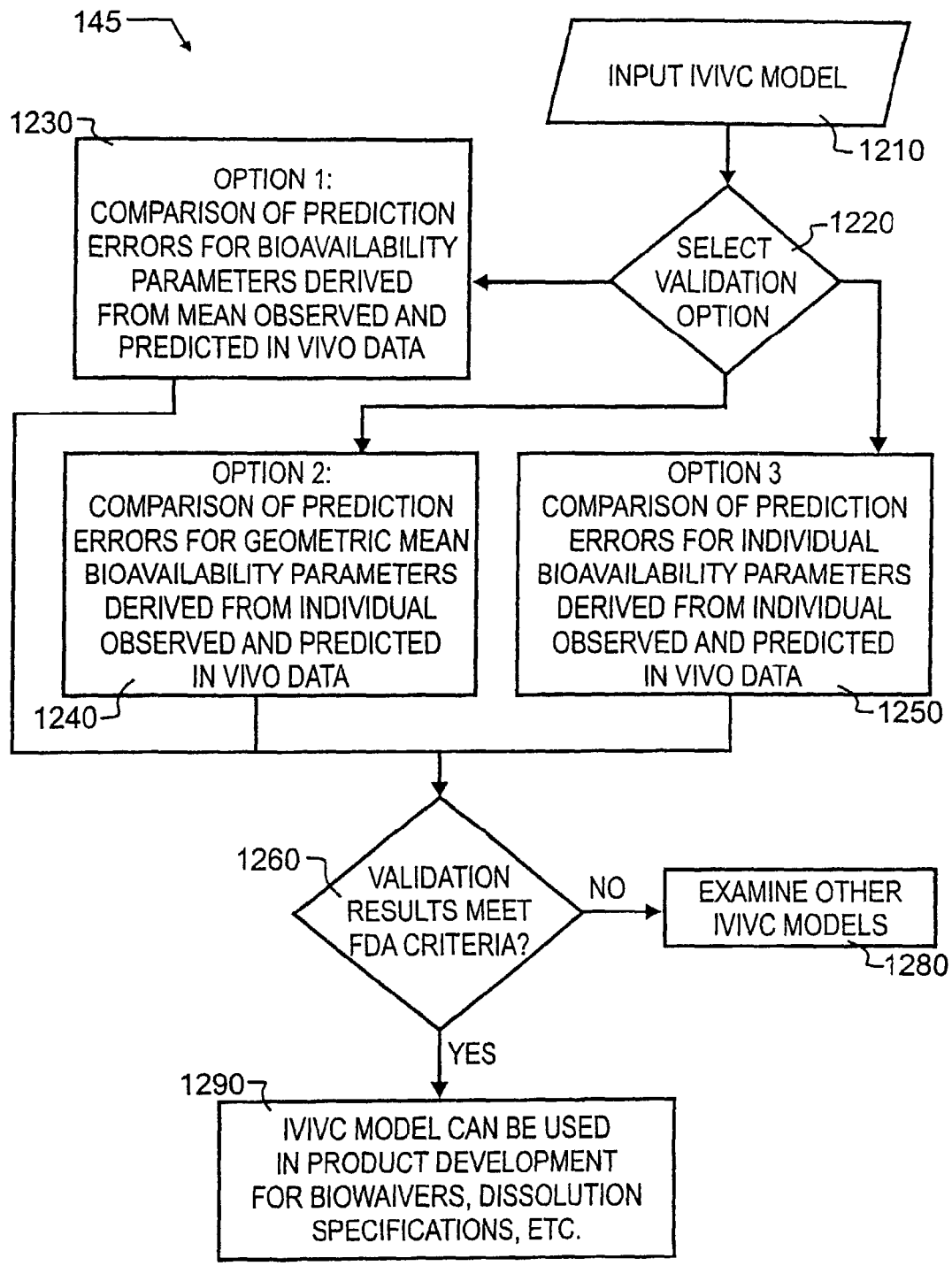
FIG. 12 illustrates in greater detail the preferred process for external validation of the IVIVC model in FIG. 1.

FIG. 12 illustrates in greater detail the preferred process for external validation of the IVIVC model in FIG. 1. Depending on the intended application of an IVIVC and the therapeutic index of the drug, evaluation of prediction error internally and/or externally may be appropriate. Evaluation of internal predictability is based on the initial data used to define the IVIVC model. Evaluation of external predictability is based on additional test data sets. In external validation process 145, the evaluation relates to how well the model predicts data when one or more additional test data sets are used that differ from those used to define the correlation. The additional test data sets used for the external prediction error calculation may have several differing characteristics compared to the data sets used in IVIVC development. Although formulations with different release rates provide the optimal test of an IVIVC's predictability, a formulation need not be prepared solely for this purpose. In the absence of such a formulation, data from other types of formulations may be considered. In each case, bioavailability data should be available for the data set under consideration.

As shown in FIG. 12, the first step 1210 is to input the IVIVC model. Next, the user will be required to select a validation option. The first option 1230 is a comparison of prediction errors for bioavailability parameters derived from mean observed and predicted in vivo data. This option is illustrated in more detail in FIG. 13. The second option 1240 is the comparison of prediction errors for geometric mean bioavailability parameters derived from individual observed and predicted in vivo data. This option is illustrated in more detail in FIG. 14. The third option 1250 is the comparison of prediction errors for individual bioavailability parameters derived from individual observed and predicted in vivo data. This option is illustrated in more detail in FIG. 15. Regardless of the option which is appropriate, the next step is to verify that the validation results meet FDA criteria in step 1260. If not, the user will need to examine other IVIVC models in step 1280. If the validation results meet FDA criteria in step 1260, then the IVIVC model can be used in product development for biowaivers, dissolution specifications, etc. as shown in step 1290.

Figure 13:
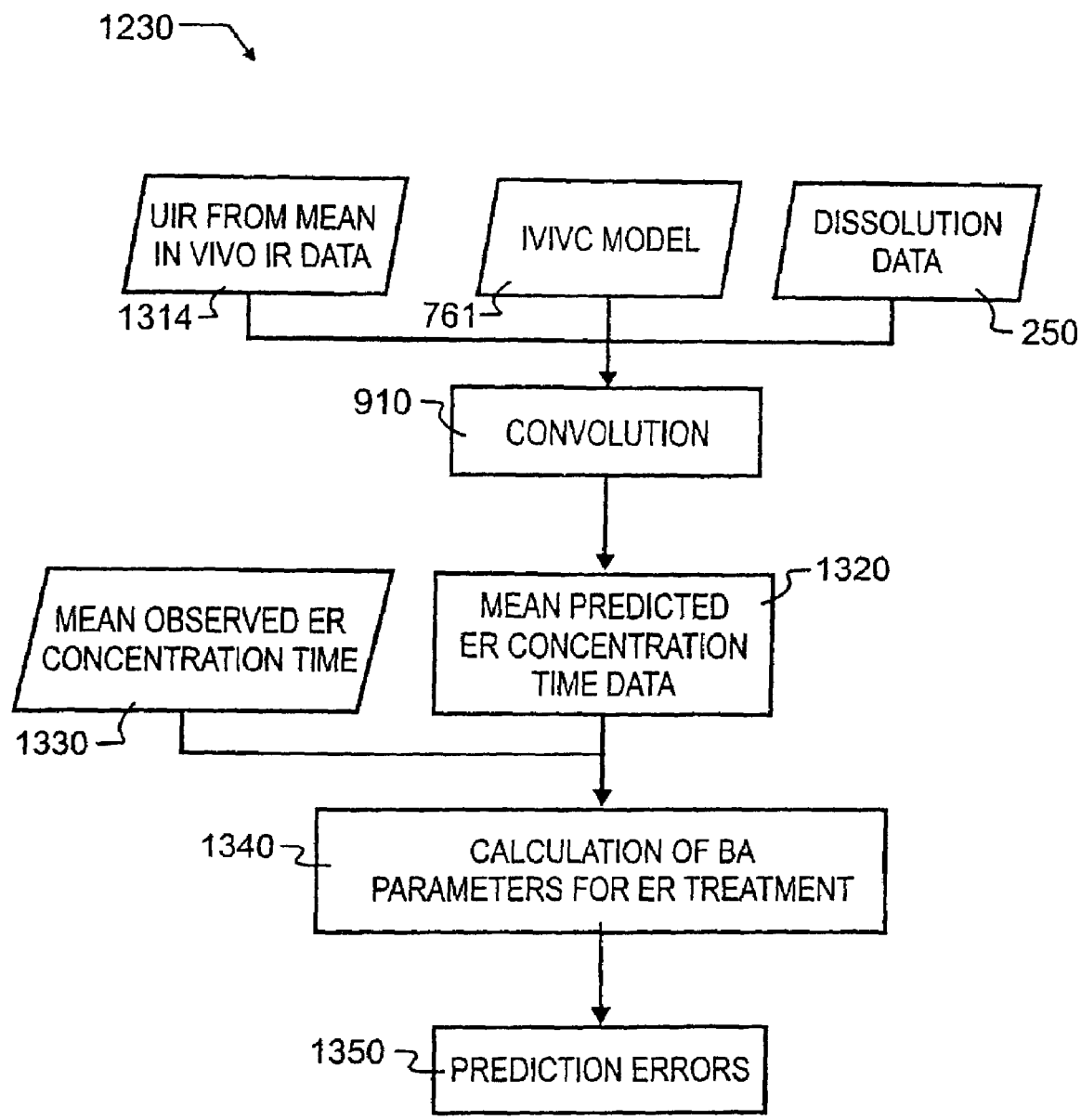
FIGS. 13–15 illustrate in greater detail the preferred validation options identified in FIG. 12.
Figure 14:
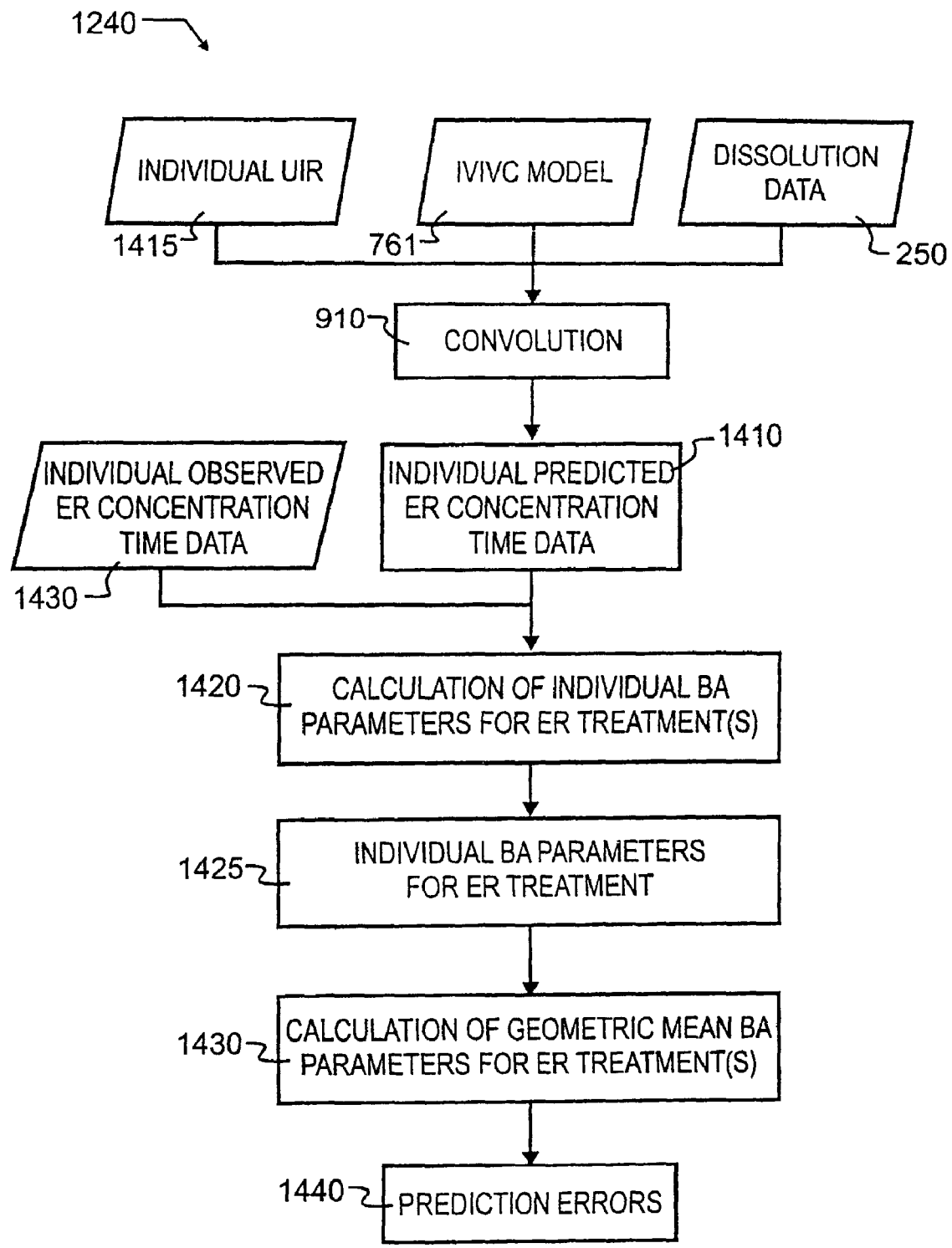
Figure 15:
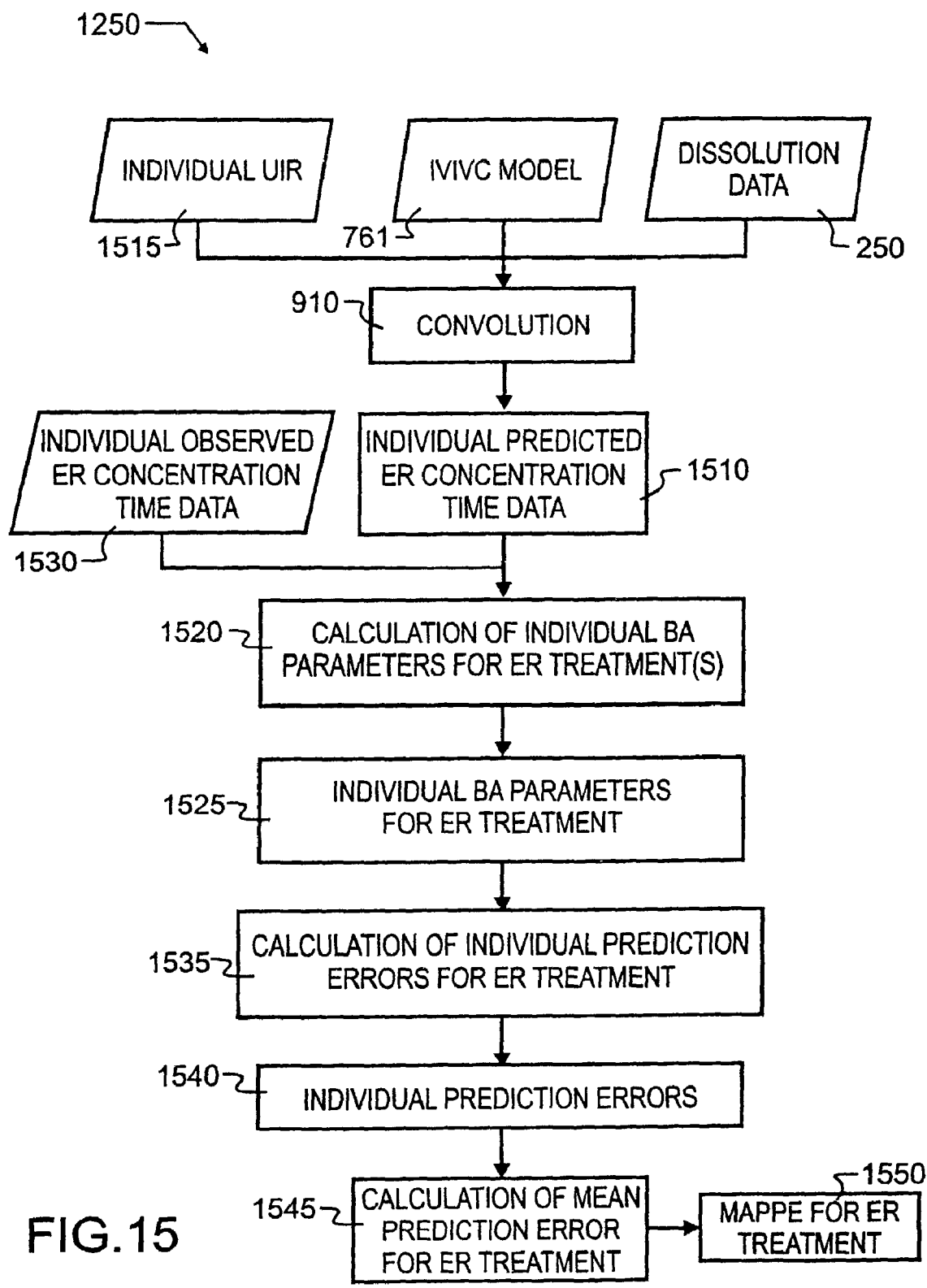

FIGS. 13–15 illustrate in greater detail the preferred validation options identified in FIG. 12. The first option 1230 shown in FIG. 13 is a comparison of prediction errors for bioavailability parameters derived from mean observed and predicted in vivo data. Using the process illustrated in this option, a UIR 1314 which may differ from UIR 114 is provided, along with the IVIVC model 761 accepted at step 760 to be validated, and the in vitro dissolution data 250 to be processed in convolution step 910 to provide mean predicted ER concentration time data 1320. The mean predicted ER concentration time data 1320 and mean observed ER concentration time data 1330 are used in step 1340 for the calculation of bioavailability (BA) parameters for ER treatment(s). The result of these calculations 1340 are prediction errors 1350, which are used in the decision whether to validate the IVIVC model. One preferred collection of data values includes CMAX and AUC values, both predicted and observed, the ratios of the predicted values to observed, and the absolute prediction errors.

The second option 1240 is the comparison of prediction errors for geometric mean bioavailability parameters derived from individual observed and predicted in vivo data, illustrated in FIG. 14. Using the process illustrated in this option, the individual UIR 1415, the IVIVC model 761 accepted at step 760 to be validated, and the in vitro dissolution data 250 are processed in convolution step 910 to provide individual predicted ER concentration time data 1410. The individual predicted ER concentration time data 1410 and individual observed ER concentration time data 1430 are used in step 1420 for the calculation of individual bioavailability parameters for ER treatment(s). The result of these calculations 1420 are individual BA parameters for ER treatment(s) 1425. The individual BA parameters for ER treatment(s) 1425 are in turn used in the calculation of geometric mean BA parameters for ER treatment(s) at step 1430, which in turn produces prediction errors 1440.

The third option 1250 is the comparison of prediction errors for individual bioavailability parameters derived from individual observed and predicted in vivo data, illustrated in FIG. 15. Using the process illustrated in this option, the individual UIR 1515, the IVIVC model 761 accepted at step 760 to be validated, and the in vitro dissolution data 250 are processed in convolution step 910 to provide individual predicted ER concentration time data 1510. The individual predicted ER concentration time data 1510 and individual observed ER concentration time data 1530 are used in step 1520 for the calculation of individual bioavailability parameters for ER treatment(s). The result of these calculations 1520 are individual BA parameters for ER treatment(s) 1525. The individual BA parameters for ER treatment(s) 1525 are in turn used in the calculation of individual prediction errors for ER treatment(s) at step 1535, which in turn produces individual prediction errors 1540. These individual prediction errors 1540 are used in the calculation of the mean prediction error for ER treatment(s) in step 1545, and then the result is used for a map for ER treatment(s) at step 1550.

In one preferred embodiment, the criteria for establishing internal predictability of the IVIVC model is that the absolute percent prediction error (% PE) to be 10% or less for $C_{max}$ and AUC. In addition, the % PE for each formulation should not exceed 15%. If these criteria are not met, the internal predictability of the IVIVC is inconclusive and evaluation of external predictability of the IVIVC should be performed as a final determination of the ability of the IVIVC to be used as a surrogate for bioequivalence.

Figure 16:
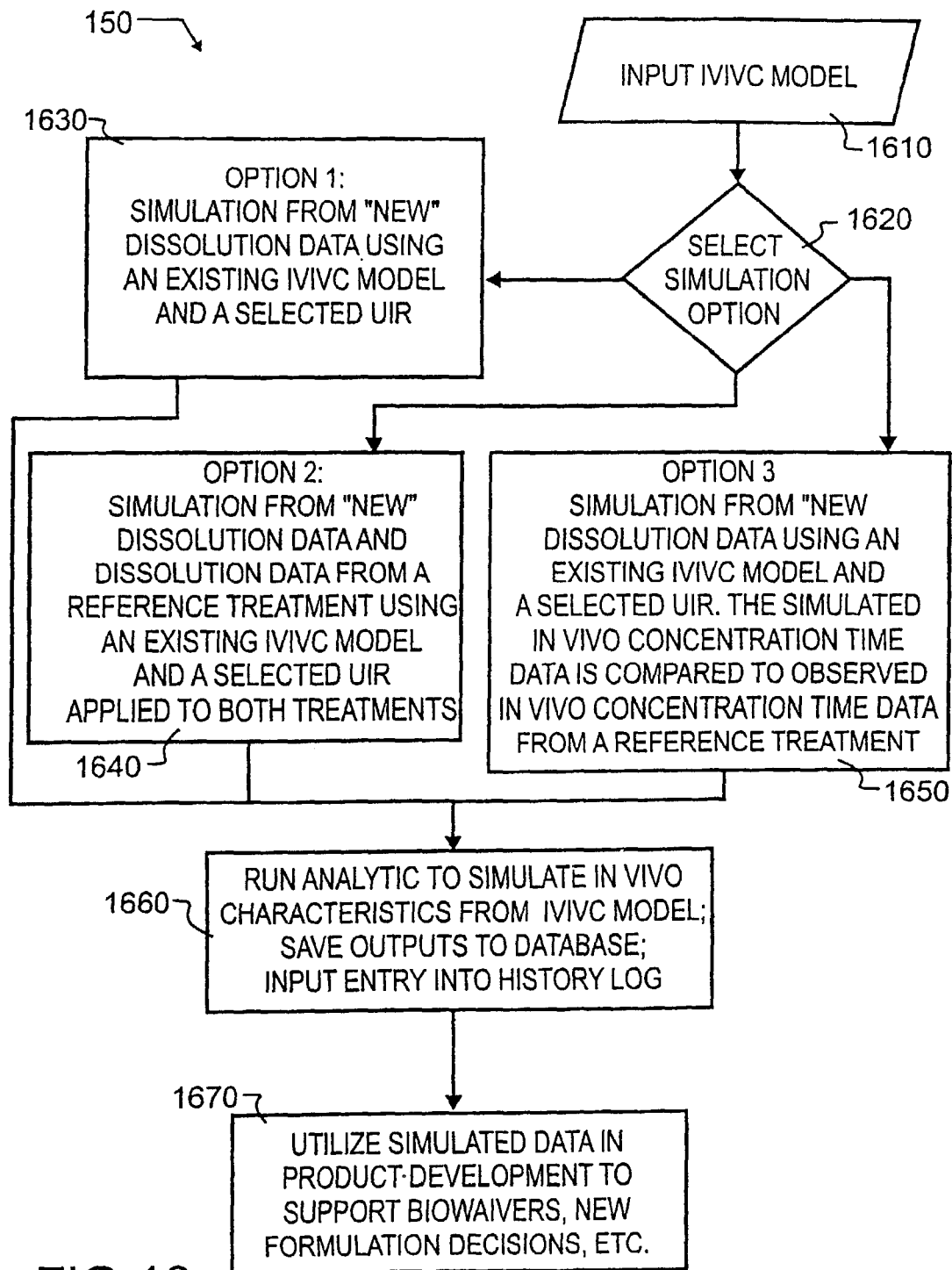
FIG. 16 illustrates in greater detail the preferred process for prediction of in vivo characteristics from in vitro data identified in FIG. 1.

FIG. 16 illustrates in greater detail the preferred process 150 for prediction of in vivo characteristics from in vitro data, first identified in FIG. 1. This prediction process 150 allows the user to predict in vivo concentration-time profiles and their associated bioavailability parameters using a pre-existing or assumed IVIVC model and in vitro dissolution data. This approach can be used to provide support for a biowaiver or SUPAC submission or to aid in the formulation selection process and study design before pharmacokinetic or clinical studies. As shown in FIG. 16, the first step 1610 is to input the IVIVC model. Next, the user will be required to select a simulation option at step 1620. The first option 1630 is a simulation from "new" dissolution data using an existing IVIVC model and a selected unit impulse response. This option is illustrated in more detail in FIG. 17. The second option 1640 is a simulation from "new" dissolution data and dissolution data from a reference treatment using an existing IVIVC model and a selected unit impulse response applied to both treatments. This option is illustrated in more detail in FIG. 18. The third option 1250 is a simulation from "new" dissolution data using an existing IVIVC model and a selected unit impulse response. The simulated in vivo concentration time data is compared to observed in vivo concentration time data from a reference treatment. This option is illustrated in more detail in FIG. 19. Regardless of the option which is appropriate, the next step after the option is to run the analytic to simulate in vivo characteristics from the IVIVC model; save outputs to the database; and input an entry into the history log, each in step 1660. The final step 1670 is to use the simulated data in product development to support biowaivers, new formulation decisions, etc. One preferred collection of data values includes $C_{max}$, AUC, and $T_{max}$ values, predicted and observed, and the ratios of the predicted to observed values.

Figure 17:
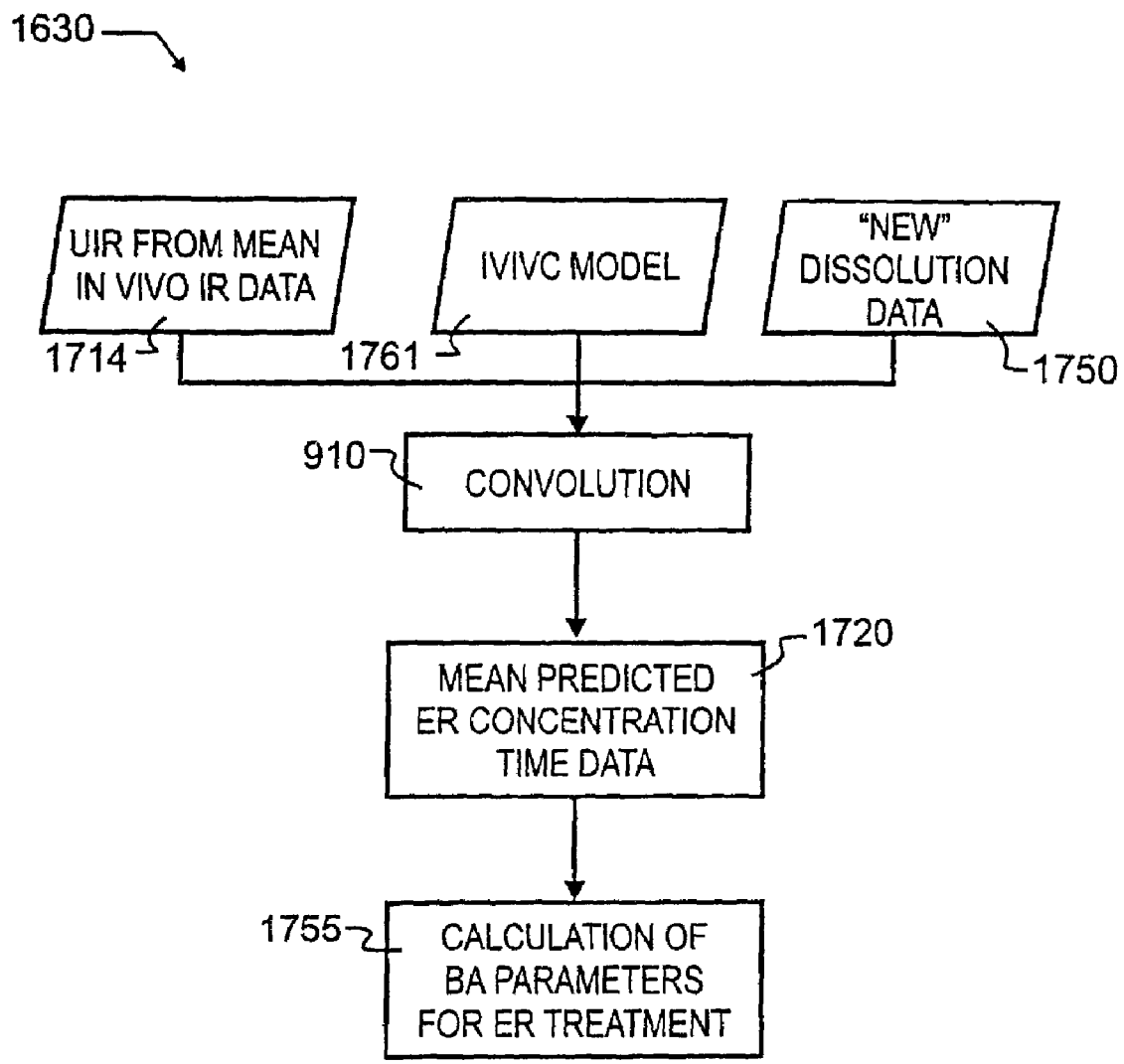
FIGS. 17–19 illustrate in greater detail the preferred simulation identified in FIG. 16.
Figure 18:
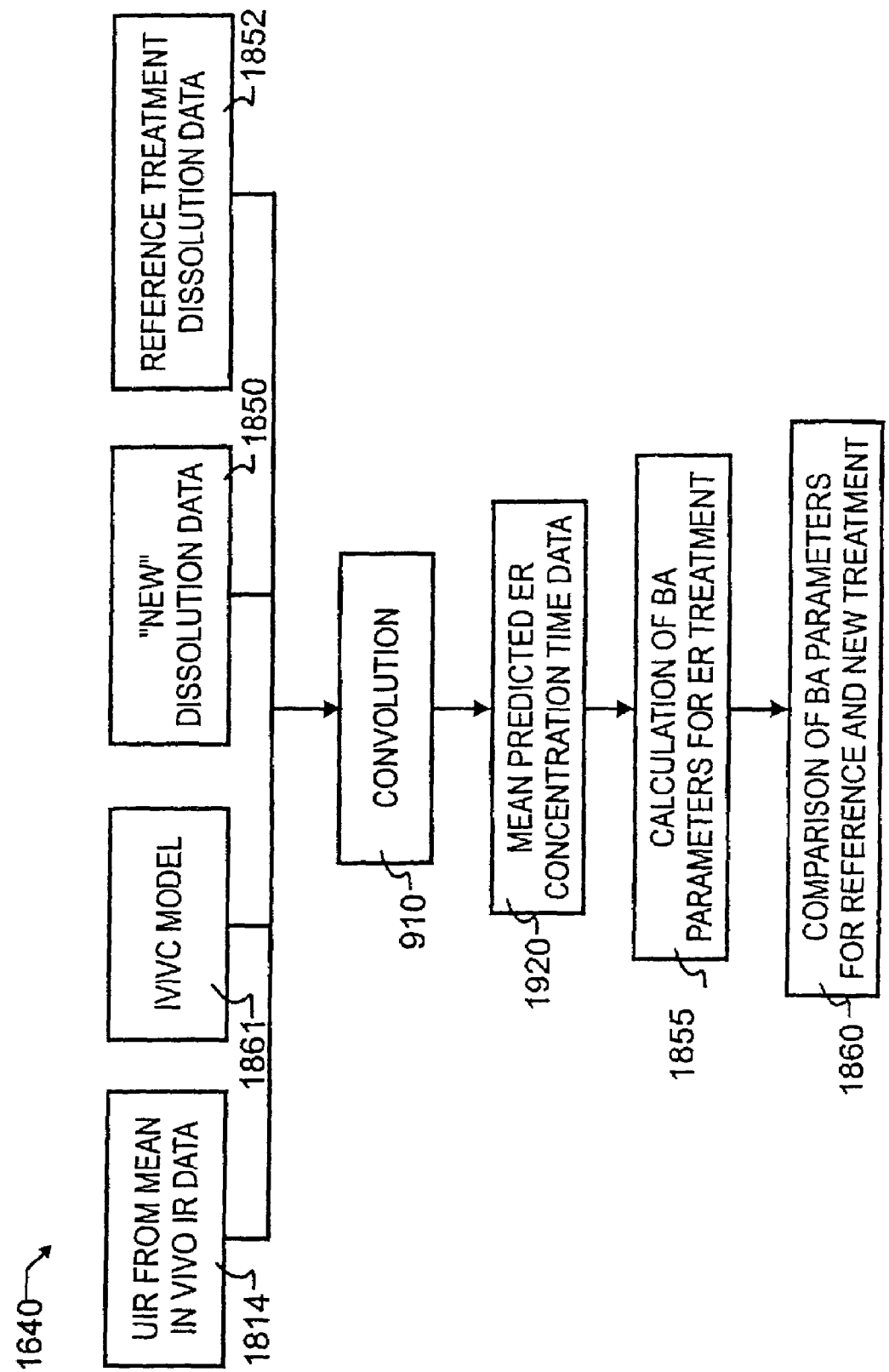
Figure 19:
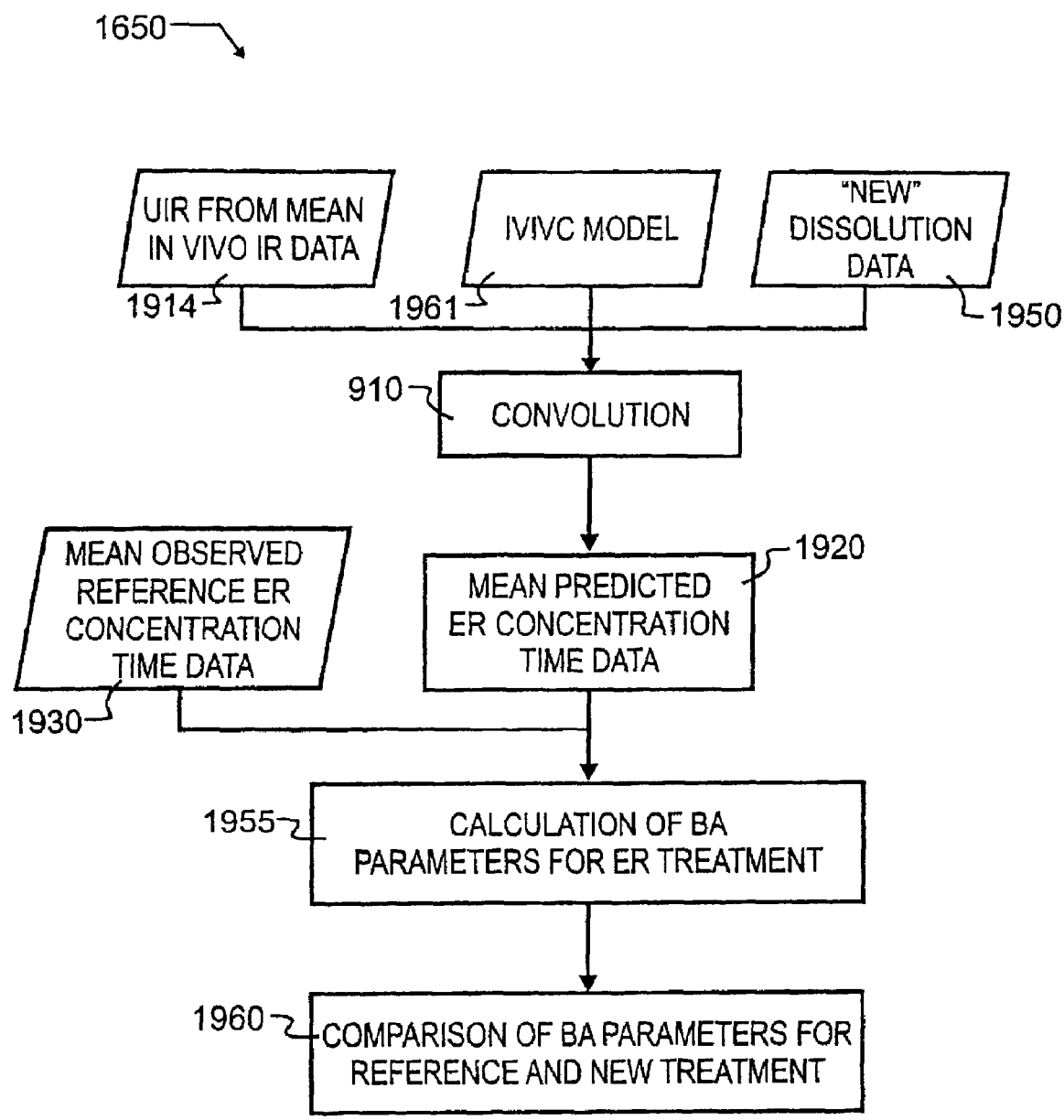

FIGS. 17–19 illustrate in greater detail the preferred prediction options identified in FIG. 16. The first option 1630 shown in FIG. 17 is a simulation from "new" dissolution data using an existing IVIVC model and a selected unit impulse response. Using the process illustrated in this option, a UIR 1714 from mean in vivo IR data is provided, along with a pre-existing or assumed IVIVC model 1761, and "new" in vitro dissolution data 1750, to be processed in convolution step 910 to provide mean predicted ER concentration time data 1720. The calculation of bioavailability parameters for ER treatment is then completed in step 1755.

The second option 1640 is a simulation from "new" dissolution data and dissolution data from a reference treatment using an existing IVIVC model and a selected unit impulse response applied to both treatments, illustrated in FIG. 18. Using the process illustrated in this option, a UIR 1814 from mean in vivo IR data is provided, along with a pre-existing or assumed IVIVC model 1861, "new" in vitro dissolution data 1850, and reference treatment dissolution data 1852 to be processed in convolution step 910. Convolution step 910 provides mean predicted ER concentration time data 1820. The calculation of bioavailability parameters for ER treatment is then completed in step 1855. In step 1860, comparison of BA parameters is made for reference and new treatment.

The third option 1650 is a simulation from "new" dissolution data using an existing IVIVC model and a selected unit impulse response, illustrated in FIG. 19. The simulated in vivo concentration time data is compared to observed in vivo concentration time data from a reference treatment. This option is illustrated in more detail in FIG. 19. Using the process illustrated in this option, a UIR 1914 from mean in vivo IR data is provided, along with a pre-existing or assumed IVIVC model 1961 and "new" in vitro dissolution data 1950, to be processed in convolution step 910. Convolution step 910 provides mean predicted ER concentration time data 1920. The calculation of bioavailability parameters for ER treatment is then completed in step 1955. In step 1960, comparison of BA parameters is made for reference and new treatment.

Figure 20:
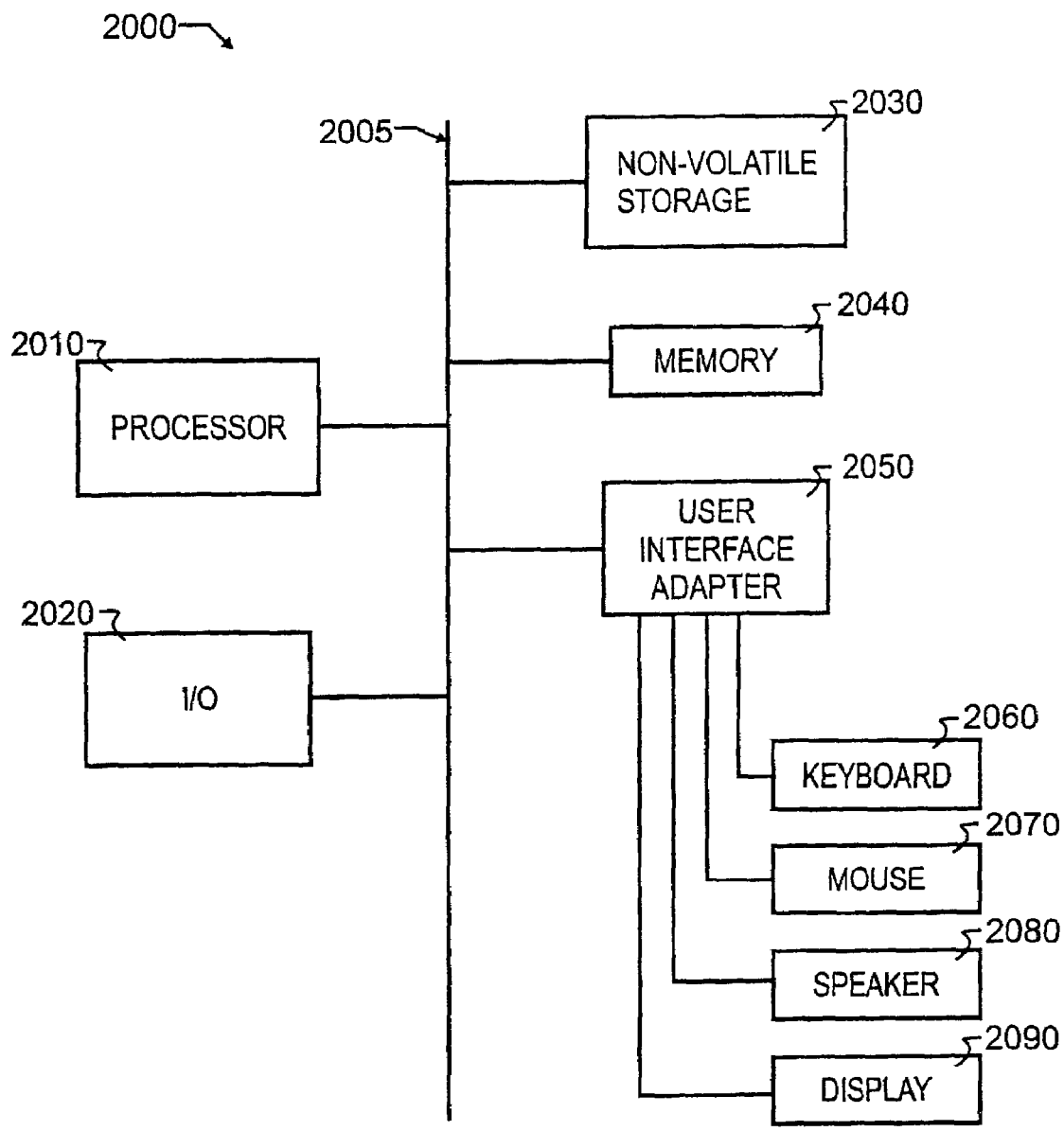
FIG. 20 illustrates a preferred apparatus for implementing the preferred methods of FIGS. 1–19.

FIG. 20 illustrates a preferred apparatus 2000 for implementing the preferred methods of FIGS. 1–19. The present method in the preferred embodiment is stored as a computer instruction set or software program in non-volatile storage 2030 or through a network or remote location via input/output (I/O) 2020. The instructions are most preferably executed by a processor 2010 utilizing memory 2040 for data storage required during program execution. Processor 2010 may take many forms, including a single microprocessor or dedicated controller, a central processing unit (CPU), one or more sets of parallel processors, one or more reduced instruction set controllers (RISC), distributed processors which are either local or distributed through a network, a neural network, or any of the others of the myriad of known processing techniques. The results are preferred to be conveyed to a user using standard user interface technology through one or more user interface adapters 2050 which in turn provide the electronic communication a keyboard 2060, mouse 2070, speaker 2080 and display 2090 and processor 2010. Communication between components comprising computer system 2000 occurs along a databus 2005, which may be a set of copper circuit traces on a circuit board, a network or any of a myriad of other signal communications structures. Nevertheless, the use of a particular hardware, apparatus or structure is not critical to the invention, provided there is an efficient means of carrying out the requisite steps of the invention.

Advantageously, according to a preferred embodiment, preferred embodiment IVIVC pharmacokinetic modeling and analysis method 100 is written using a programming language that allows for platform independence such that it may be executed on any of a variety of user computing apparatus 200 having different operating systems. As known in the art, Fortran, Java and Perl are examples of programming languages optimized for cross-platform computing, though other languages will be recognized as suitable for the execution of the preferred method 100.

Preferably, the user interface will comprise software for driving a menu-driven, multi-window graphical interface which will allow the user to easily manipulate and analyze data in one or more simultaneous viewer windows. In a preferred embodiment, the user interface is adapted to provide the look and feel of an Internet browser interface, a Windows 95/98/2000/ME/XP interface, a KDE interface, or other X-Windows type interface. In a most preferred embodiment, IVIVC pharmacokinetic modeling and analysis method 100 is implemented as a web application, using a web server to provide a user access to stored software, models and analytics. In this implementation, a user will gain access through a secure website with a firewall and SSL encryption. 21 CFR Part 11 compliance is ensured by the use of electronic signatures and an electronic audit trail, referred to herein above as the history log. During any session, the program generates an electronic audit trail of all operations conducted in a project, including user identification and date and time stamps. The log can not be edited but can be exported as a text file. New data can be input into the system by uploading files, or through interactive input such as from keyboard 2060.

Having thus disclosed the preferred embodiment and some alternatives to the preferred embodiment, additional possibilities and applications will become apparent to those skilled in the art without undue effort or experimentation. Therefore, while the foregoing details what is felt to be the preferred embodiment of the invention, no material limitations to the scope of the claimed invention are intended. Further, features and design alternatives that would be obvious to one of ordinary skill in the art are considered to be incorporated herein. Consequently, rather than being limited strictly to the features recited with regard to the preferred embodiment, the scope of the invention is set forth and particularly described in the claims hereinbelow.

We claim:

1. A computer executable model of a biological system in combination with a computer system including a memory and a processor, said computer executable model comprising:

a plurality of biological representations stored in said memory and having a plurality of chemical level data points, each said chemical level data point representing a level of a chemical within a particular time period in a biological component;

a means for determining unit impulse response from a first collection of said plurality of biological representations;

a means for performing deconvolution having as inputs said unit impulse response and a second collection of said plurality of biological representations and producing as an output in vivo mean absorption data;

a means for developing an in vitro in vivo correlation model having as inputs a third collection of said plurality of biological representations, each of said third collection of said plurality of biological representations chemical level data points representing in vitro ER data and said in vivo mean absorption data; and a means for validation of said in vitro in vivo correlation model.

2. The computer executable model of a biological system in combination with a computer system of claim 1, wherein said means for developing an in vitro in vivo correlation model further comprises a means for time-scaling at least on of said third collection of said plurality of biological representations and said in vivo mean absorption data to enable said third collection of said plurality of biological representations and said in vivo mean absorption data to be superimposed upon a graph.

3. The computer executable model of a biological system in combination with a computer system of claim 1, wherein said means for developing an in vitro in vivo correlation model further comprises a means for time-shifting at least one of said third collection of said plurality of biological representations and said in vivo mean absorption data to enable said third collection of said plurality of biological representations and said in vivo mean absorption data to be superimposed upon a graph.

4. The computer executable model of a biological system in combination with a computer system of claim 1, wherein said means for developing an in vitro in vivo correlation model further comprises a means for adjusting said developing means to compensate for bioavailability differences between said third collection of said plurality of biological representations and said in vivo mean absorption data to enable said third collection of said plurality of biological representations and said in vivo mean absorption data to be superimposed upon a graph.

5. The computer executable model of a biological system in combination with a computer system of claim 1, wherein said means for developing an in vitro in vivo correlation model further comprises a means for adjusting said developing means to compensate for release rate differences between said third collection of said plurality of biological representations and said in vivo mean absorption data to enable said third collection of said plurality of biological representations and said in vivo mean absorption data to be superimposed upon a graph.

6. The computer executable model of a biological system in combination with a computer system of claim 1, wherein said means for developing an in vitro in vivo correlation model further comprises a means for imposing a limit on a gastrointestinal absorption duration to enable said third collection of said plurality of biological representations and said in vivo mean absorption data to be superimposed upon a graph.

7. The computer executable model of a biological system in combination with a computer system of claim 1, wherein said means for determining unit impulse response further comprises:

means to select a treatment from the group that is identified as having faster release than the ER treatments to be used in the deconvolution;

means to identify whether a dosage regimen is a single or multiple dose regimen;

means to choose one of a mean approach or an individual approach;

means to execute a polyexponential function estimated to describe pharmacokinetic characteristics; and means to save results from said executing means to a database.

8. The computer executable model of a biological system in combination with a computer system of claim 7, wherein said polyexponential function estimated to describe pharmacokinetic characteristics is approximated by:

$$c\delta(t) = \Sigma i\ ai\ \exp(\alpha i(t-t0)), t \geq t0 \quad (1)$$

;;

$$c\delta(t) = 0, t < t0 \quad (2)$$

where t0 is a common lag time.

9. The computer executable model of a biological system in combination with a computer system of claim 1, wherein said means for developing an in vitro in vivo correlation model further comprises a means to fit a linear regression model to said in vitro ER data and said in vivo mean absorption data of the following form:

$$X_{vivo(t)} = \begin{cases} 0 & t < 0 \\ & u = t \text{ for } t \leq T \\ a_1 + a_2 \cdot X_{vitro}(-b_1 + b_2 \cdot u) & u = T \text{ for } t > T \end{cases}$$

where:

Xvivo(t) represents a % release in vivo at time (t);

a1 allows for a difference between the initial in vitro and in vivo drug release;

a2 represents the bioavailability of the extended release formulation relative to immediate release;

b1 allows for a time shift between in vitro and in vivo release;

b2 allows for time scaling between in vitro and in vivo release; and

T represents a time after which no drug absorption occurs.

10. The computer executable model of a biological system in combination with a computer system of claim 1, wherein said means for developing an in vitro in vivo correlation model further comprises a means to plot exploratory plots to estimate initial conditions in the IVIVC model.

11. A method for processing biological profile data for in vitro in vivo correlation comprising the steps of:

storing a plurality of biological profiles in a computer memory in computer readable form, each biological signal profile in ones of said plurality of biological signal profiles comprising a plurality of data points, each data point representing a measurement of a chemical level;

determining a unit impulse response from an at least first one of said biological profiles;

performing deconvolution on an at least second one of said biological profiles using said unit impulse response and producing in vivo mean absorption data;

developing an in vitro in vivo correlation model using said in vivo mean absorption data and an in vitro ER data biological signal profile; and validating said in vitro in vivo correlation model.

12. The method for processing biological profile data for in vitro in vivo correlation of claim 11 wherein said step of developing an in vitro in vivo correlation model further comprising the steps of:
- inputting said in vitro ER data biological signal profile and said in vivo mean absorption data;
- running analytics to generate correlation data representative of said in vitro ER data biological signal profile and said in vivo mean absorption data;
- plotting said correlation data;
- selecting IVIVC model initial default values;
- executing said IVIVC model to produce results;
- reviewing said IVIVC model results; and
- determining whether said IVIVC model is within FDA guidelines.

13. The method for processing biological profile data for in vitro in vivo correlation of claim 12 wherein said plotting step further comprises forming a plot of exploratory plots to estimate initial conditions in the IVIVC model.

14. The method for processing biological profile data for in vitro in vivo correlation of claim 12 further comprising the step of deciding whether a weighting factor is added to said IVIVC model.

15. The method for processing biological profile data for in vitro in vivo correlation of claim 12 further comprising the steps of:
- saving IVIVC model outputs to a computer memory; and
- inputting an entry into a history log.

16. The method for processing biological profile data for in vitro in vivo correlation of claim 15 further comprising the step of refining said IVIVC model initial default values responsive to said FDA guidelines determining step.

17. The method for processing biological profile data for in vitro in vivo correlation of claim 11 wherein said validating step further comprises a comparison of prediction errors for bioavailability parameters derived from mean observed and predicted in vivo data.

18. The method for processing biological profile data for in vitro in vivo correlation of claim 11 wherein said validating step further comprises a comparison of prediction errors for geometric mean bioavailability parameters derived from individual observed and predicted in vivo data.

19. The method for processing biological profile data for in vitro in vivo correlation of claim 11 wherein said validating step further comprises a comparison of prediction errors for individual bioavailability parameters derived from individual observed and predicted in vivo data.

20. The method for processing biological profile data for in vitro in vivo correlation of claim 11 further comprising the step of predicting in vivo characteristics from in vitro data.

21. The method for processing biological profile data for in vitro in vivo correlation of claim 11 wherein said step of performing deconvolution further comprises the step of choosing whether one or more of said at least second one of said biological profiles are to be selected.

22. The method for processing biological profile data for in vitro in vivo correlation of claim 21 wherein said at least first one of said biological profiles comprises individual data for an individual subject, and said at least second one of said biological profiles comprises individual in vivo data for an individual subject.

23. The method for processing biological profile data for in vitro in vivo correlation of claim 22 wherein said at least first one of said biological profiles further comprises at least one study of multiple subject data, and said at least second one of said biological profiles further comprises at least one study of multiple subject data, and step of performing deconvolution further comprises selecting between said multiple subject data and said individual subject data.

* * * * *